US008366682B2

(12) United States Patent
Wyrick

(10) Patent No.: US 8,366,682 B2
(45) Date of Patent: Feb. 5, 2013

(54) MEDICINE INJECTION APPARATUSES

(75) Inventor: Ronald E. Wyrick, Spokane, WA (US)

(73) Assignee: Washington Biotech Corporation, Spokane, WA (US)

( * ) Notice: Subject to any disclaimer, the term of this patent is extended or adjusted under 35 U.S.C. 154(b) by 369 days.

(21) Appl. No.: 12/380,954

(22) Filed: Mar. 4, 2009

(65) Prior Publication Data

US 2010/0228193 A1 Sep. 9, 2010

(51) Int. Cl.
*A61M 5/00* (2006.01)
(52) U.S. Cl. .................................................. 604/235
(58) Field of Classification Search .............. 604/117, 604/156–157, 232–236, 246, 218, 151–152
See application file for complete search history.

(56) References Cited

U.S. PATENT DOCUMENTS

| | | |
|---|---|---|
| 1,718,701 A | 6/1929 | O'Sullivan |
| 2,168,686 A | 8/1939 | Saffir |
| 3,055,362 A | 9/1962 | Uytenbogaart |
| 3,252,446 A | 5/1966 | Bateman |
| 3,572,336 A | 3/1971 | Hershberg |
| 3,605,742 A | 9/1971 | Tibbs |
| 3,605,744 A | 9/1971 | Dwyer |
| 3,882,863 A | 5/1975 | Sarnoff et al. |
| 3,910,444 A | 10/1975 | Foster |
| 3,982,651 A | 9/1976 | Braun et al. |
| 4,031,893 A | 6/1977 | Kaplan et al. |
| 4,044,933 A | 8/1977 | Artz |
| 4,226,235 A | 10/1980 | Sarnoff et al. |
| 4,365,390 A | 12/1982 | Kageyama et al. |
| 4,367,737 A | 1/1983 | Kozam et al. |
| 4,394,863 A | 7/1983 | Bartner |
| 4,578,064 A | 3/1986 | Sarnoff et al. |
| 4,658,830 A | 4/1987 | Sarnoff |
| 4,723,937 A | 2/1988 | Sarnoff et al. |
| 4,795,433 A | 1/1989 | Sarnoff |
| 5,078,680 A | 1/1992 | Sarnoff |
| 5,085,641 A | 2/1992 | Sarnoff et al. |
| 5,092,842 A | 3/1992 | Bechtold et al. |
| 5,102,393 A | 4/1992 | Sarnoff et al. |

(Continued)

FOREIGN PATENT DOCUMENTS

| | | |
|---|---|---|
| EP | 1 958 654 | 8/2008 |
| EP | 2067496 A1 | 10/2009 |

(Continued)

OTHER PUBLICATIONS

WO PCT-US2010-000682 Search Rept., Aug. 2, 2010, Washington Biotech Corporation.

(Continued)

*Primary Examiner* — Nicholas Lucchesi
*Assistant Examiner* — Melissa A Snyder
(74) *Attorney, Agent, or Firm* — Wells St. John P.S.

(57) ABSTRACT

Medicine injection apparatuses having multiple chambers. The chambers may be in lateral relationship. A torsional part is adapted to turn and be repositioned angularly relative to a main body to allow different chambers to be used to receive an injection assembly. The medicine injector can be constructed to administer multiple doses. The apparatuses may also have a storage chamber for storing the injection assembly after use. Plural drivers may be used to administer multiple doses, such as at the different angular positions of the torsional part. The apparatuses may allow multiple automatic injections from different angular positions and storage of an injector after use. Needle fright is reduced by minimizing exposure of an injection needle prior to injection.

20 Claims, 31 Drawing Sheets

U.S. PATENT DOCUMENTS

| | | | |
|---|---|---|---|
| 5,137,516 A | | 8/1992 | Rand et al. |
| 5,147,323 A | * | 9/1992 | Haber et al. .......... 604/191 |
| 5,176,643 A | | 1/1993 | Kramer et al. |
| 5,232,459 A | | 8/1993 | Hjertman |
| 5,267,963 A | | 12/1993 | Bachynsky |
| 5,358,489 A | | 10/1994 | Wyrick |
| 5,417,326 A | | 5/1995 | Winer |
| 5,540,664 A | | 7/1996 | Wyrick |
| D375,789 S | | 11/1996 | Bryant et al. |
| 5,578,014 A | | 11/1996 | Erez et al. |
| 5,584,815 A | * | 12/1996 | Pawelka et al. .......... 604/191 |
| 5,665,071 A | | 9/1997 | Wyrick |
| 5,695,472 A | | 12/1997 | Wyrick |
| 5,722,956 A | | 3/1998 | Sims et al. |
| 5,833,669 A | | 11/1998 | Wyrick |
| 6,068,421 A | | 5/2000 | Pierpont |
| 6,210,369 B1 | | 4/2001 | Wilmot et al. |
| 6,312,412 B1 | * | 11/2001 | Saied et al. .......... 604/191 |
| 6,387,078 B1 | | 5/2002 | Gillespie, III |
| 6,405,912 B2 | | 6/2002 | Giannou |
| 6,478,780 B1 | | 11/2002 | Shields |
| 6,508,801 B1 | | 1/2003 | Fineberg |
| 6,562,002 B1 | | 5/2003 | Taylor et al. |
| 6,595,362 B2 | | 7/2003 | Penney et al. |
| 6,613,017 B1 | | 9/2003 | Mickley |
| 6,641,015 B2 | | 11/2003 | Huggins, Jr. |
| 6,678,014 B1 | | 1/2004 | Jin et al. |
| 6,726,649 B2 | | 4/2004 | Swenson et al. |
| 6,796,963 B2 | | 9/2004 | Carpenter et al. |
| 6,986,760 B2 | | 1/2006 | Giambattista et al. |
| 7,297,136 B2 | | 11/2007 | Wyrick |
| 7,931,618 B2 | | 4/2011 | Wyrick |
| 2001/0030196 A1 | | 10/2001 | Stull et al. |
| 2003/0004467 A1 | | 1/2003 | Musick et al. |
| 2003/0014018 A1 | | 1/2003 | Giambattista et al. |
| 2003/0106824 A1 | | 6/2003 | Wilmot et al. |
| 2004/0039336 A1 | | 2/2004 | Amark et al. |
| 2004/0069667 A1 | | 4/2004 | Tomellini et al. |
| 2004/0133159 A1 | | 7/2004 | Haider et al. |
| 2004/0182736 A1 | | 9/2004 | Mesa et al. |
| 2004/0211806 A1 | | 10/2004 | Wilkerson et al. |
| 2005/0148933 A1 | | 7/2005 | Raven et al. |
| 2005/0187519 A1 | | 8/2005 | Harris et al. |
| 2006/0129122 A1 | | 6/2006 | Wyrick |
| 2007/0017532 A1 | | 1/2007 | Wyrick |
| 2007/0017533 A1 | | 1/2007 | Wyrick |
| 2007/0031619 A1 | | 2/2007 | Mirabell |
| 2008/0214996 A1 | | 9/2008 | Kimmell et al. |

FOREIGN PATENT DOCUMENTS

| | | |
|---|---|---|
| TW | 155687 | 4/1991 |
| WO | WO 94/27660 | 12/1994 |
| WO | WO 99/30759 A2 | 6/1999 |
| WO | WO 03099358 A2 | 12/2003 |

OTHER PUBLICATIONS

WO PCT-US2010-000682 Written Opin, Aug. 2, 2010, Washington Biotech Corporation.

WO PCT/US10/000682 IPRP, Sep. 6, 2011, Washington Biotech Corporation.

WO PCT/US05/43309 IPER, Nov. 15, 2006, Washington Biotech Corporation.

WO PCT/US05/43309 Search Report, Jun. 22, 2005, Washington Biotech Corporation.

WO PCT/US05/43309 Written Opinion, Jul. 5, 2006, Washington Biotech Corporation.

WO PCT/US05/44159 IPRP, Jun. 13, 2007, Washington Biotech Corporation.

WO PCT/US05/44159 Search Report, Feb. 28, 2006, Washington Biotech Corporation.

WO PCT/US05/44159 Written Opinion, Mar. 3, 2006, Washington Biotech Corporation.

WO PCT/US05/44190 IPRP, Jun. 13, 2007, Washinton Biotech Corporation.

WO PCT/US05/44190 Search Report, May 13, 2006, Washington Biotech Corporation.

WO PCT/US05/44190 Written Opinion, May 15, 2006, Washington Biotech Corporation.

WO PCT/US06/07097 IPRP, Jan. 10, 2008, Washington Biotech Corporation.

WO PCT/US06/07097 Search Report, Mar. 1, 2007, Washington Biotech Corporation.

WO PCT/US06/07097 Written Opinion, Mar. 2, 2007, Washington Biotech Corporation.

AAAAI. "Position Statement: Anaphylaxis in Schools and Other Child-Care Settings," http://www.aaaai.org/media/resources/academy_statements/position_statements/ps34.asp Jun. 23, 2003, pp. 1-6.

EP 05853152.6-1265 Supplementary Search Report dated Feb. 5, 2008.

Korenblat, P. et al., "A Retrospective Study of Epinephrine Administration for Anaphylaxis: How Many Doses Are Needed?", Allergy Asthma Proc. 1999; 20:383-386.

Merck Manual, 17th Ed., 1053-1054 (1999).

Sampson, H.A. et al., "Fatal and Near-Fatal Anaphylactic Reactions to Food in Children and Adolescents," N. Engl. J. Med. 1992;327:380-394.

Sampson, H.A., "Anaphylaxis and Emergency Treatment," Pediatrics 111:1601-1608 (2003).

Taiwan Patent Application 0941319817 Preliminary Examination Report dated Dec. 10, 2007.

* cited by examiner

MEDICINE INJECTION APPARATUSES

INCORPORATION BY REFERENCE

Applicant hereby incorporates by reference U.S. Pat. No. 7,297,136 issued Nov. 20, 2007 which is incorporated in full without claim to priority therefrom.

BACKGROUND INFORMATION

There is a significant market in medicine autoinjectors. Such devices are often used to inject a medicine like epinephrine to treat allergic reactions from bee stings or other anaphylactic episodes.

Other medications are or may be needed on a quick basis. Autoinjectors may serve useful for quick access and administration of other medicines. Alternative medicines include medicines now available, such as some analgesics. It may further include medicines which may be available or found hereafter to be suitable for administration using autoinjectors. Such alternative medicines might include antidotes to various poisons. Such antidotes may be used to counter the effects of poison gas attack, such as may be used in military operations. Other possible uses which may be now known or hereafter developed, might include antidotes for snake bites, other poisonous animals, and poisonous plants. Exposure to poison gases or biological agents in wartime or other situations may in particular be best treated when there is immediate injection of a suitable injectable medicine.

Other medications may also be suitable for administration in autoinjectors, such as pain relievers, vaccines needed on a quicker basis than usually provided via medical services facilities, and other medicines provided on an unexpected basis or those only useful for a short period of time. Autoinjectors may also be desired for other reasons, such as: remoteness, travel, convenience at sea where motion may make more traditional injections more difficult, and many other reasons. Use of autoinjectors may be desired with many medications which are injectable.

Some problems which have been associated with autoinjectors is that the number of doses of medicine being injected may not be the same for different people, different sizes of people (children versus adults who typically require different dosing), and the circumstances giving rise to the need for medicine injection may require different dosing levels. Prior efforts to effect dose control have not been altogether successful in meeting all the various situations and people for which medicine injection is needed.

Another longstanding problem arises from the need in the use of some drugs for an immediately available second dose or further multiple doses if the first dose has been unsuccessful in treating the medical emergency. Heretofore a user requiring immediately available second or subsequent automatically injected doses of medication was forced to carry two or more autoinjectors. This has lead to unnecessary expense and inconvenience due to the bulk of carrying multiple injectors. Further the potential for inadvertently leaving one or more of the necessary injectors at home or elsewhere leads to potential critical risk.

In the use of epinephrine for anaphylaxis for example, studies have shown that approximately one third of patients requiring epinephrine will need a second dose within a few minutes, while other studies have shown that only approximately sixteen percent in fact carry the necessary second autoinjector. Therefore an autoinjector that is capable of delivering multiple automatic injections would meet a critical need which has not been successfully met in prior devices.

A further longstanding problem which arises in almost all injection of medicines is that many people find the process unpleasant. This may be further aggravated by obvious visual sighting of the syringe to the patient. This may also be a problem for another user which is merely an administrator. The administration of an injection to a recipient or patient may be unpleasant or uncomfortable both for the patient to perform self-administration, and for performance by an available other administrative person. This may be a problem leading to delay in the administration of an injection. Thus, it is desirable to minimize these negative reactions, since many people are strongly affected by them and just about all people desire avoiding them except due to acceptance as a needed medical treatment.

The inventor has determined that, it is desirable to have medicine injectors which may controllably administer one or more doses and minimize visual exposure of the injection needle. It is also desirable to have an autoinjector which may provide multiple automatically injected doses, and which can do such in a manner which minimizes adverse effects associated with visual sighting of the needle, particularly during the time period immediately before the injection or injections occur. This may apply to situations as indicated above or in other circumstances.

It is more generally desirable to reduce or minimize negative reactions associated with injections and to reduce sighting of injection needles. Reducing negative effects is particularly desirable immediately before an injection is administered.

Due to the nature of certain medicines and sensitivity of some individuals, it is also desirable to provide penetration depth control for the injection needle. This may also be desired for proper administration at the appropriate depth in the tissue or person, or for other reasons.

Some or all of the problems explained above and other problems may be helped or solved by one or more embodiments of the inventions shown and described herein. Such inventions may also be used to address other problems not set out above or which are only understood or appreciated at a later time. The future may also bring to light currently unknown or unrecognized benefits which may be appreciated or more fully appreciated in association with the inventions shown and described herein. The desires and expected benefits explained herein are not admissions that others have recognized such prior to the inventions described herein.

BRIEF DESCRIPTION OF THE DRAWINGS

Preferred forms, configurations, embodiments and/or diagrams relating to and helping to describe preferred aspects and versions of the inventions are explained and characterized herein, often with reference to the accompanying drawings. The drawings and all features shown therein also serve as part of the disclosure of the inventions of the current document, whether described in text or merely by graphical disclosure alone. Such drawings are briefly described below.

DETAILED DESCRIPTION

Figure 1:
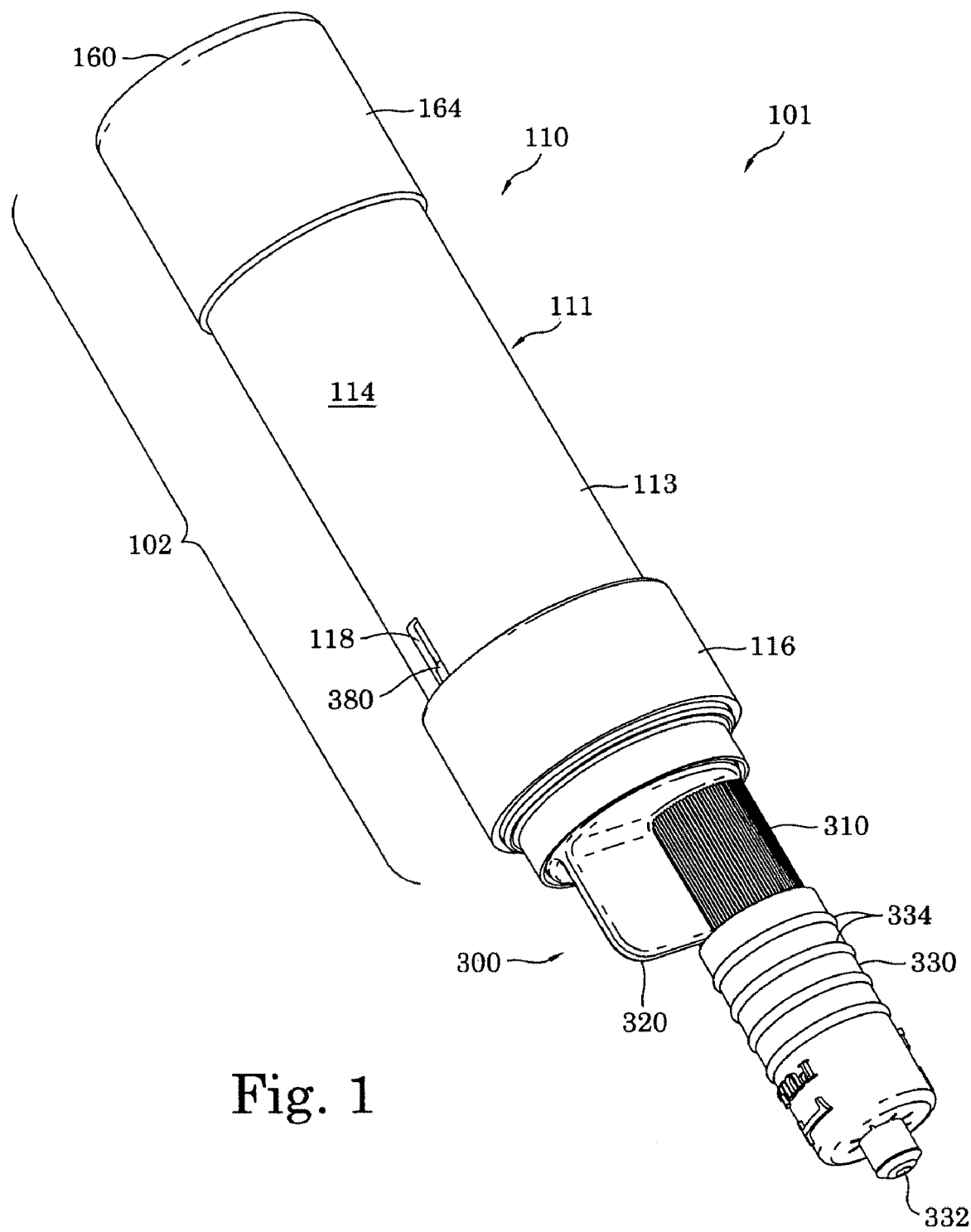
FIG. 1 is a perspective view of a currently preferred best mode embodiment according to the inventions hereof.

A table of sections of this detailed description follows.

TABLE OF DETAILED DESCRIPTION SUBSECTIONS

BRIEF DESCRIPTION OF THE DRAWINGS
INTRODUCTORY NOTES
GENERAL OVERVIEW OF APPARATUS
UPPER OUTER BODY
    Main Outer Body Piece
    Upper End of Main Body Piece
    Safety Apertures and Safeties
TOP CAP
INNER BODY PIECE
    Side Walls
    Upper End
    Chambers Generally and Partitions
    First Chamber
    Second Chamber
    Third Chamber
LONGITUDINAL GUIDES BETWEEN INNER AND OUTER BODY PIECES FIRST DRIVER ASSEMBLY
    Driver Shaft Piece
    Driver Spring
    Driver Safety
    First Driver Trigger
SECOND DRIVER ASSEMBLY
INJECTION ASSEMBLY
    Medicine Ampoule
    Needle Module
    Plunger Assembly
    Injection Assembly Length Adjuster
    Dose Limiter
TORSIONAL ASSEMBLY
    Generally and Torsion Main Piece
    Torsional Latch or Retraint
    Injector Extension or Extensions
    Sheath Remover
    Injection Needle Sheath
    Injector Retractor or Return Spring
    Torque Application Features
    Penetration Controller
COUPLING OR COUPLER
MULTIPLE MEDICINE INJECTORS
    Generally
    Connection of Multiple Units for Portability
METHODS AND MANNERS OF USING AND OPERATING
    Overview of Summary of Operation
    Pre-Injection Conditions and Factors
    Firing of First Dose
    Repositioning to Second Stage
    Torsional or Angular Latching and Movement
    Removal of Dose Limiter
SECOND STAGE RELATED MATTERS
    Latching
    Injection Assembly
    Second Driver Related Actions
    Third Stage Operation
    Reinstallation of Sheath Remover Cap
    Reinstallation of Safety End Cap -continued

TABLE OF DETAILED DESCRIPTION SUBSECTIONS

Disposal of Spent Injector
  METHODS AND MANNER OF MAKING
    Outer Body Piece(s)
    Inner Body Piece(s)
    Safety End Cap
    Injection End Cap
    Torsion Part
    Coupler
    Drivers
    Second Safety
    Injection Assembly
    Return Spring
    Miscellaneous
  INTERPRETATION NOTES Introductory Notes The readers of this document should understand that the embodiments described herein may rely on terminology used in any section of this document and other terms readily apparent from the drawings and the language common therefor as may be known in a particular art and such as known or indicated and provided by dictionaries. Dictionaries were used in the preparation of this document. Widely known and used in the preparation hereof are Webster's Third New International Dictionary (© 1993), The Oxford English Dictionary (Second Edition, © 1989), and The New Century Dictionary (© 2001-2005), all of which are hereby incorporated by reference for interpretation of terms used herein and for application and use of words defined in such references to more adequately or aptly describe various features, aspects and concepts shown or otherwise described herein using more appropriate words having meanings applicable to such features, aspects and concepts.

This document is premised upon using one or more terms with one embodiment that may also apply to other embodiments for similar structures, functions, features and aspects of the inventions. Wording used in the claims is also descriptive of the inventions, and the text and meaning of the claims and abstract are hereby incorporated by reference into the description in their entirety as originally filed. Terminology used with one, some or all embodiments may be used for describing and defining the technology and exclusive rights associated herewith.

The readers of this document should further understand that the embodiments described herein may rely on terminology and features used in any suitable section or embodiment shown in this document and other terms readily apparent from the drawings and language common or proper therefor. This document is premised upon using one or more terms or features shown in one embodiment that may also apply to or be combined with other embodiments for similar structures, functions, features and aspects of the inventions and provide additional embodiments of the inventions.

General Overview of Apparatus

FIG. 1 shows a preferred medicine injection apparatus 101 according to the inventions. Apparatus 101 forms a portable autoinjector. Injection apparatus 101 has an upper or first part and a lower or second part. The upper and lower parts are assemblies that are adapted to turn relative to each other when one is rotated or twisted relative to the other.

The injection apparatus 101 has an upper body assembly 102. The upper body assembly includes an exterior body piece or assembly 110 having a main body piece 111. Within the exterior body assembly is an interior body assembly 212 (see FIG. 26). The interior body assembly houses two drivers 131 and 231 (see FIGS. 17-20) which are used to drive at least one injection assembly at two different stages of operation.

The lower part of the injection apparatus 300 is movable torsionally. As shown, it is moved in a twisting or torsional manner between three different positions. One position has the medicine injection assembly aligned with the first driver, another has it aligned with the second driver and in a third angular position the medicine injection assembly is aligned with a third chamber into which the used injection assembly can be recessed and stored after use of the apparatus.

This configuration allows a single injector to administer two doses without the recipient or other user from having the injection needle significantly exposed to viewing prior to the injection or injections. This helps to reduce needle fear which is a factor in both use and patient comfort and peace of mind.

A portion of the injection needle is viewable by looking into the barrel or when the needle sheath is removed or not present, such is less likely to induce needle fear than prior to injection. Many people are adversely affected by the sight of injection needles during an injection. The reduced visual presentation of the needle during the first injection and reduced potential for viewing during the second and subsequent injections reduces needle fear.

The apparatus 101 may be used to administer a single dose or two doses of medicines as may be needed in a particular situation. Other embodiments may provide for subsequent injections. For example, it is common for epinephrine to be administered to treat anaphylactic shock caused by allergic reaction to various instigating factors such as bee stings, food reactions, and other causes. Since the size of the person and degree of reaction may vary substantially, then in some cases a single dose is needed and in other cases two doses may be needed. The time between the first dose and any needed second dose may be critical in some situations. The importance may also vary significantly in different instances, and the apparatus may be closed for later use to administer a second or subsequent dose or doses because the second safety is independently removable and any additional stages may be similarly configured for independent operation. In such situations, after rotation to the ready position for the next stage injection, the needle sheath and sheath remover can be reinstalled until the time any such subsequent injection is needed.

Apparatus 101 may also be used to administer other medication such as analgesics, antidotes, and potentially any of a wide variety of other fluid injectable medications where one or multiple doses may be needed depending upon the situation and medication being administered. This can in one form of the inventions be done using a single administration needle and by having multiple laterally positioned chambers of a wide range of numbers and holding at least one ampoule of medicine which is repositioned in a manner similar to that described in detail below which illustrates two doses.

Although the current preferred form of the invention has chambers that are approximately aligned in parallel, other lateral relationships may also be suitable. For example an approximately conical lateral relationship might be suitable or desirable in some cases. Other configurations may in some instances be desired or merely be workable.

It should also be appreciated that in alternative embodiments (not shown) there can be multiple injection ampoules and needles used to administer one or more doses of multiple medications. For example, this may be done having a larger body and more than one injection extension.

Further details of the best mode or modes described and other alternatives and details of the apparatuses and methods according hereto are further explained herein.

Upper Outer Body

Main Outer Body Piece

Figure 12:
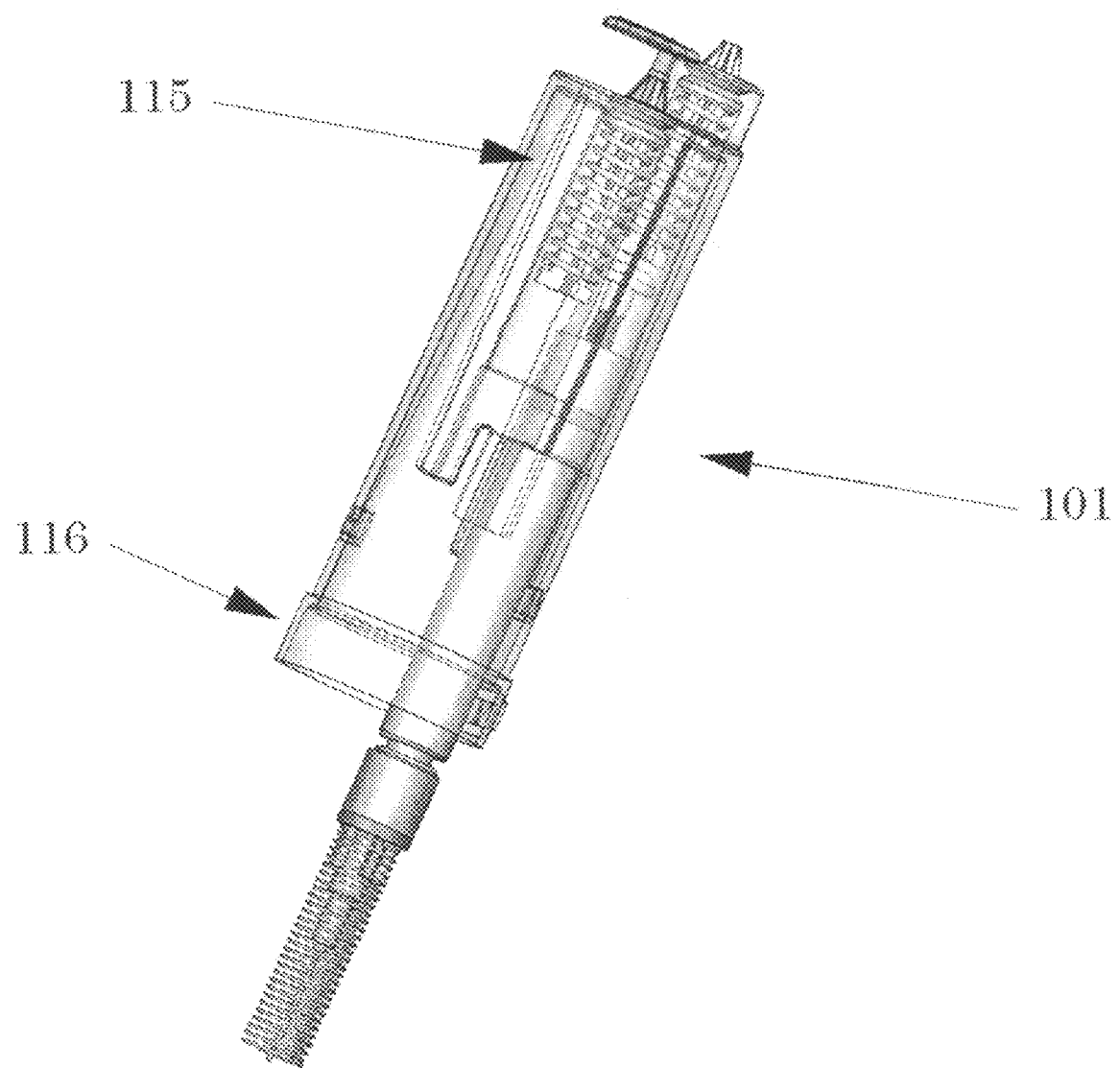
FIG. 12 is a transparent perspective view of the apparatus with the torsional part, upper cap, and lower cap removed.

FIG. 1 shows an outer body 110 having a suitably shaped main body piece 111 having a main body piece wall 113. Wall 113 has an exterior surface 114 and an interior surface 115 (see FIG. 12).

The outer body piece also preferably includes an enlarged section 116 which also has an enlarged inside diameter which forms a receiver used to receive an upper portion 152 (see FIG. 30) of coupler 150. As shown, coupler or coupling piece 150 is used to couple the torsional assembly 300 to the interior body assembly 212 (see FIG. 9).

Figure 8:
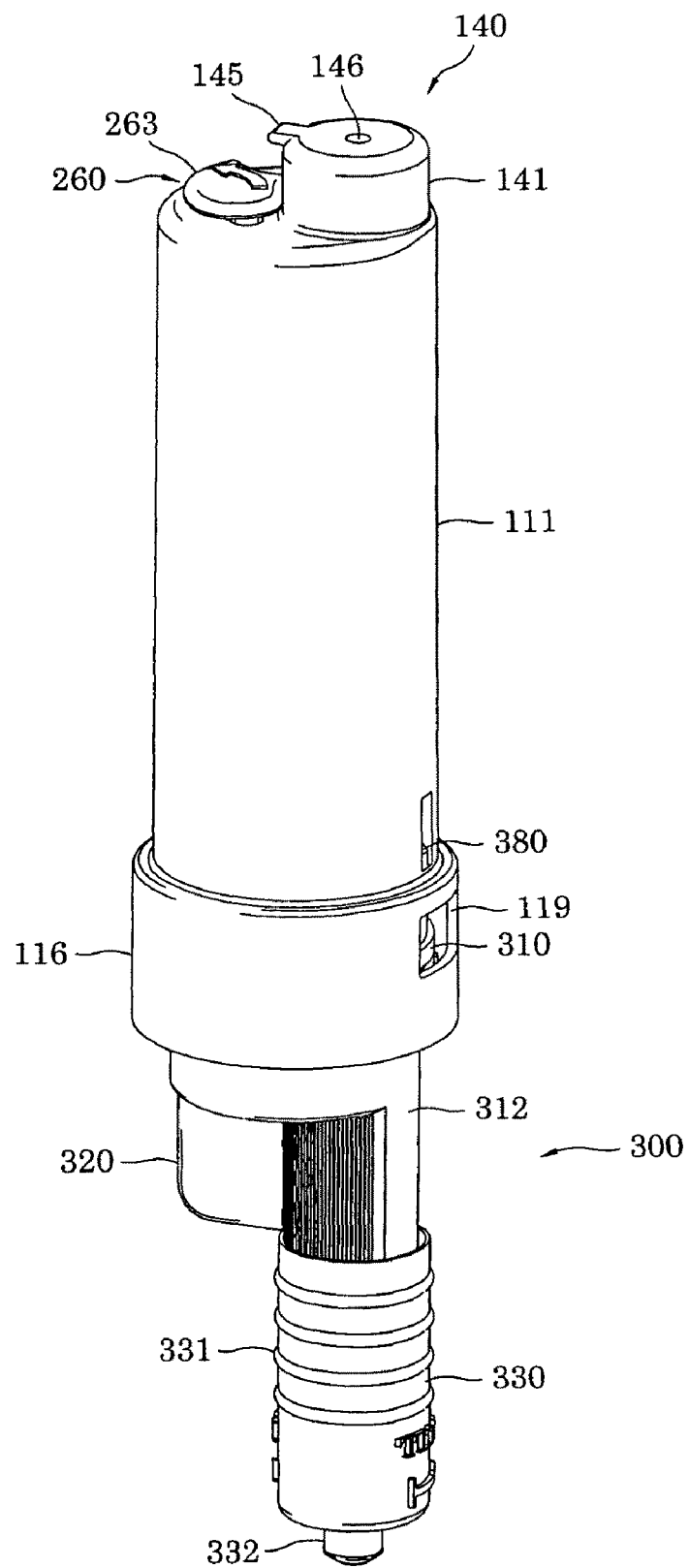
FIG. 8 is a perspective view from another viewing angle of the apparatus of FIG. 1 also with the top cap removed.

The enlarged section may also be provided with an ampoule view window 119 (FIG. 6) formed through the enlarged section 116 of the outer body piece 110 (also see FIG. 8). This allows a user to check the clarity, color or other indicator which may be a property of the medicine to make sure it is still of good quality for use before injection.

Upper End of Main Body Piece

Figure 7:
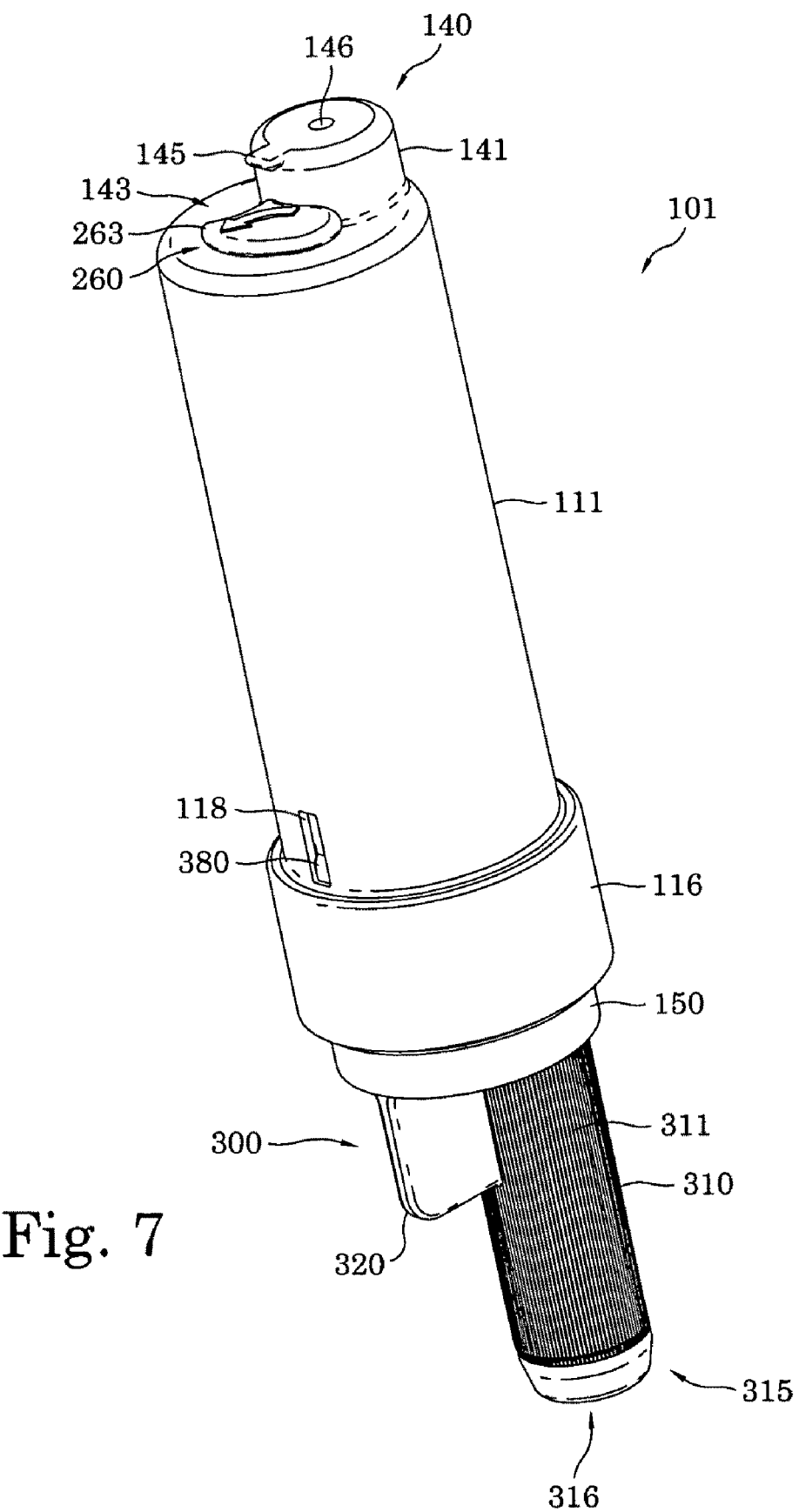
FIG. 7 is a perspective view of the apparatus of FIG. 1 with the top cap and sheath remover removed.
Figure 9:
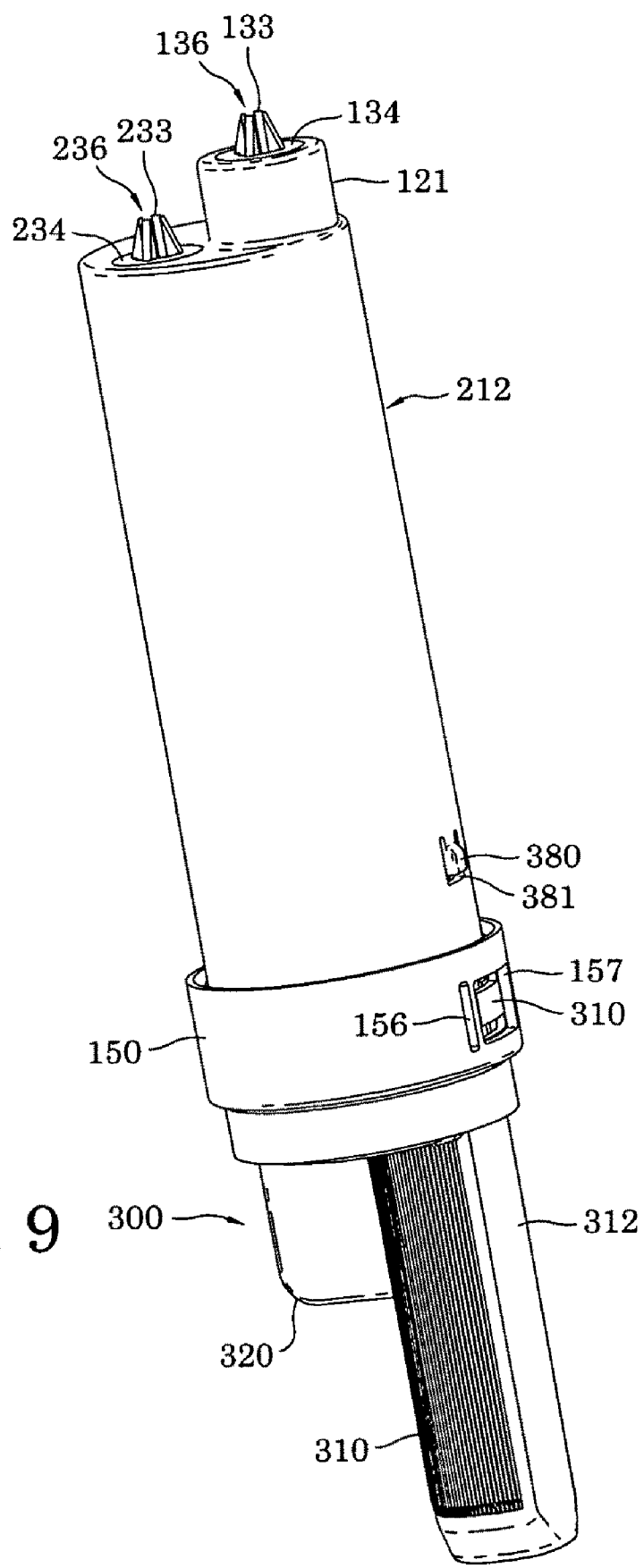
FIG. 9 is a view similar to FIG. 8 but with the outer body piece of the upper assembly removed to show the apparatus with the inner body piece without coverage by the outer body piece.

FIGS. 7-9, among others, illustrate the upper end 140 of the main body piece 111 having features used in the construction and functioning of the injection apparatus. Upper end 140 includes a first stage extension 141 which extends upwardly from the main end surface 143. The extension 141 may advantageously or optionally include a tab 145 which helps prevent unintended removal of the second stage safety piece 260.

Safety Apertures and Safeties

The upper or safety end of apparatus 101 is advantageously provided with an outer body end wall 143. The end wall is preferably provided with a first safety aperture 146 (see FIG. 7). This advantageously is upon the end of extension 141. A second safety aperture 147 (See FIG. 34) is included on the end wall 143.

The first stage extension includes a safety aperture 146. Safety aperture 146, as shown, receives a first safety pin 161 (see FIG. 6).

The second safety aperture 147 advantageously receives a second safety having a second safety pin 262 which extends thereinto.

The safety pins fit within driver center pieces 132 and 232 (see FIGS. 9, 23, 24 and 29). The driver center pieces 132 and 232 advantageously have plural barbed ends 133 and 233 that catch on driver ferrules 134 and 234. This may be at ferrule openings 135 and 235. Within the barbed pieces are preferably used to form safety openings 136 and 236 which receive the first and second safety pins 161 and 261. The second safety pin 262 may be provided with a head 263 thereon for easier manipulation. Although the first safety pin 161 may be part of cap 160 it may alternatively be a separate piece. Ferrules 134 and 234 are mounted in the end wall of the inner body piece as may be further indicated with respect to the driver description.

Top Cap

Top cap 160 has a side wall 164 and an end wall 165. The top or safety end cap has an interior chamber within such walls and an open end. The open end and portions of the interior chamber fit over the outer body piece. When the top cap is installed upon the upper part end, then the safeties are covered within the interior chamber. The first safety 161 preferably depends or extends downwardly from the top or end wall of the top cap in the illustrated embodiment. The second safety 260 is supported by the upper assembly.

Inner Body Piece

Side Walls

Figure 26:
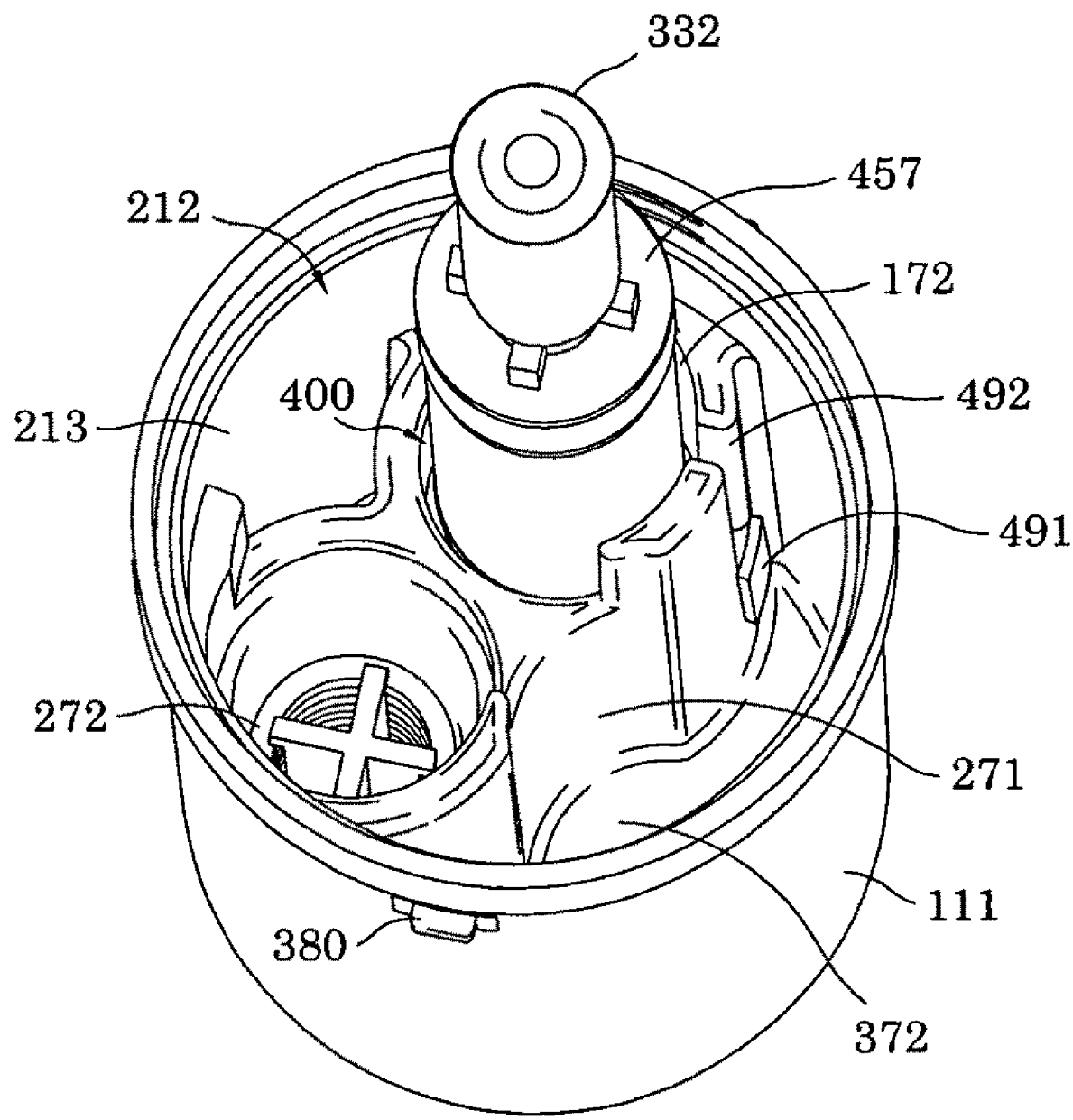
FIG. 26 is a perspective view showing the injector assembly in the upper portions of the body and a needle protector over the injection needle.
Figure 27:
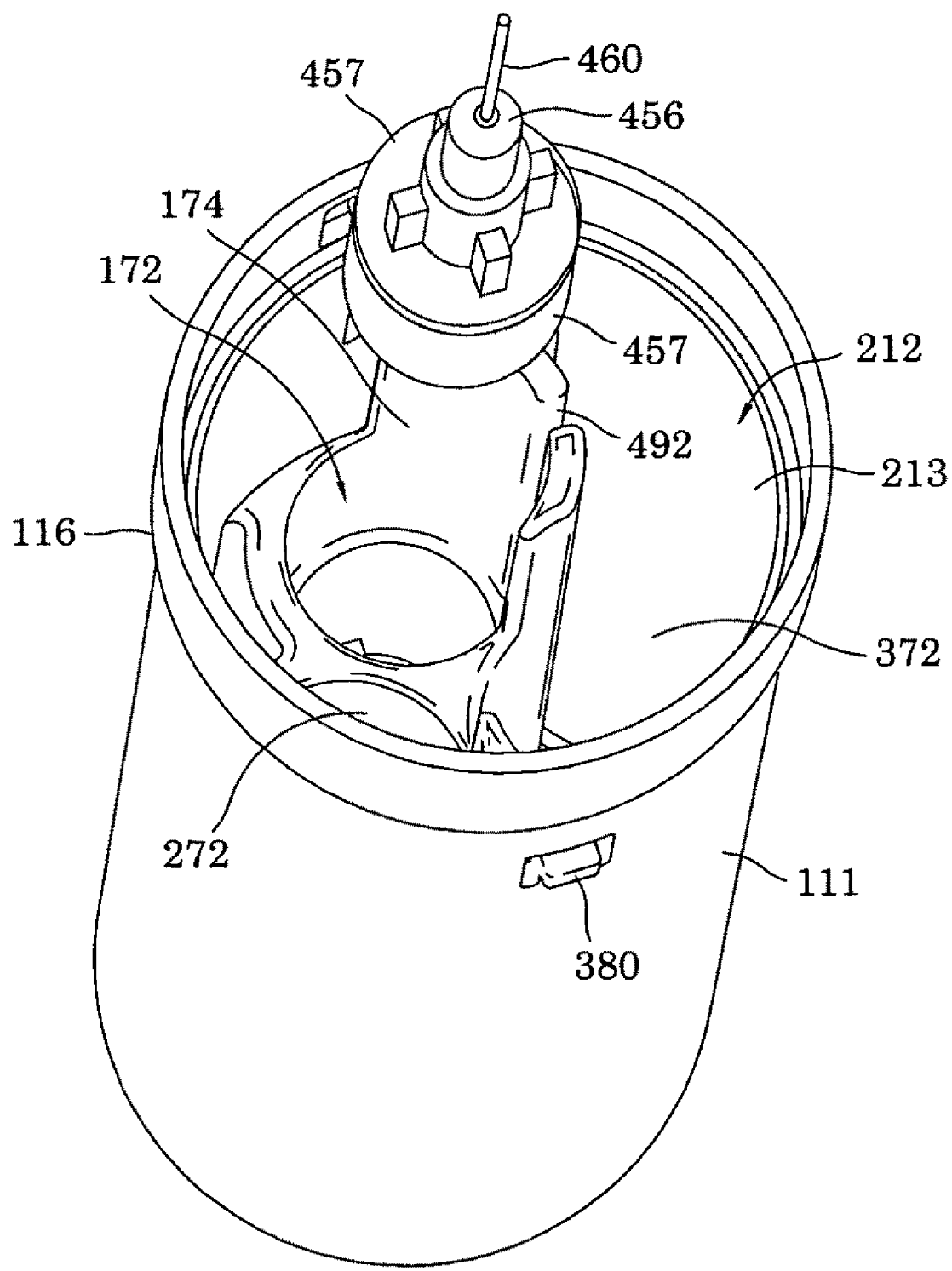
FIG. 27 is a perspective view of the assembly similar to FIG. 26 with the needle protector and ampoule removed and from a different viewing position.

The inner body assembly 212 includes a inner body piece 213 (see FIGS. 26 and 27). The inner body piece 213 has a series of features in the preferred embodiment shown which are described in greater detail herein.

Upper End

Figure 29:
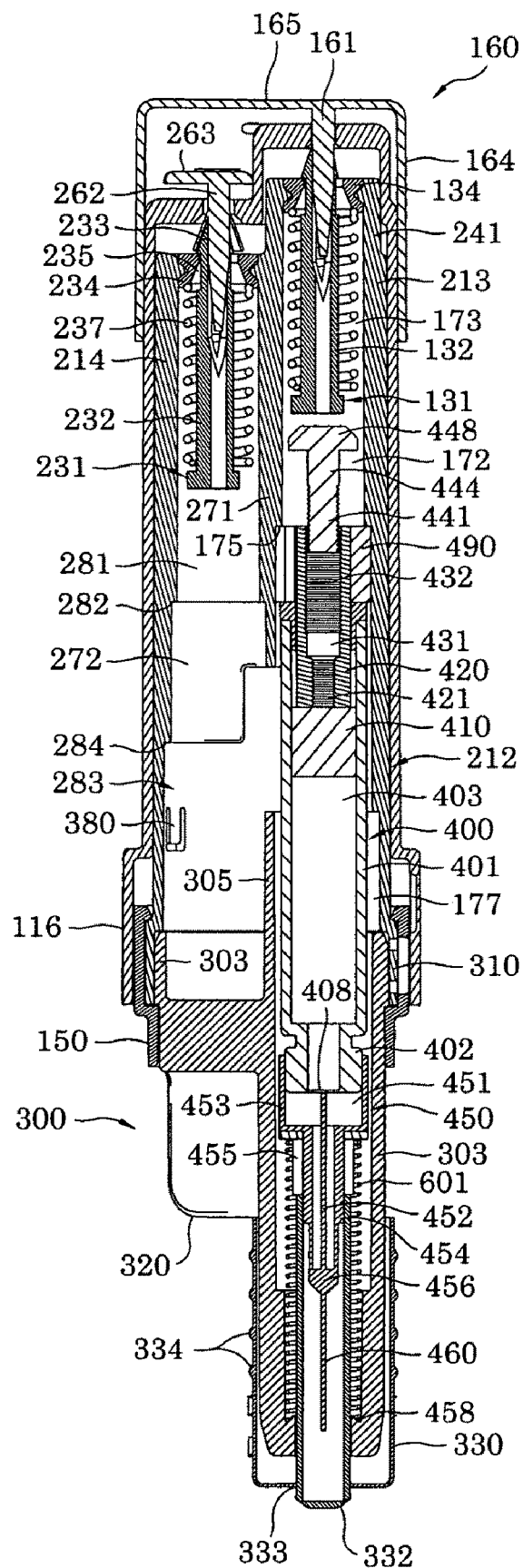
FIG. 29 is a longitudinal sectional view showing the apparatus in FIG. 1 fully assembled.

FIG. 29 and others show the upper end of inner body piece 213 has an inner body piece extension 241 which mounts ferrule 134. A lower inner body piece surface 214 holds second ferrule 234. A septum 271 (FIG. 29) extends from the upper end downwardly and includes features used in partitioning the first chamber 172, second chamber 272 and third chamber 372, respectively, as shown in FIGS. 26, 27, 29 and elsewhere.

Chambers Generally and Partitions

Figure 35:
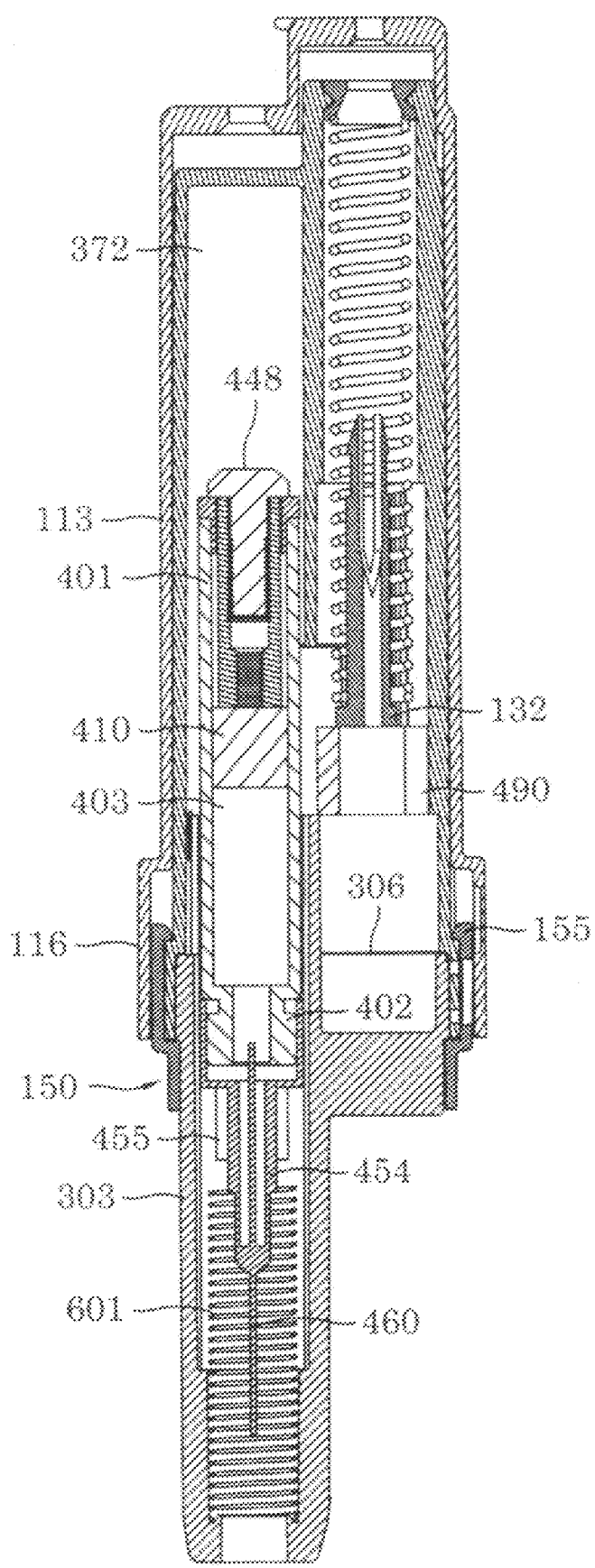
FIG. 35 shows the apparatus of FIG. 29 with the torsional part rotated to a third position and the injection or sharps assembly has been forced by the retraction spring at least partially into a third storage chamber.

FIG. 29 shows the first chamber 172 is used to initially house parts of the first driver and injection assembly for a first dose delivered by a first stage of injection operation. FIG. 29 also shows the second chamber 272 is used to house parts of the second driver and the injection assembly after repositioning thereto for any desired second dose delivered during a second injection stage of operation. FIG. 35 show the third chamber 372 is used to receive parts of the injection assembly in a third or other final stage storage condition. As shown, the injector 101 stores the injection assembly in a storage position and condition after the first injection and any second injection has been conducted. If a second injection is not needed, a second chamber might be configured to become a storage chamber.

First Chamber

First chamber 172 includes several different sections. A driver section 173 receives the first driver 131. The driver section 173 may also include sufficient length to receive a plunger extension part 444 (see FIG. 23) which is part of the injection assembly 400 described further below.

First chamber 172 also includes a second section 174 which receives a dose control piece 490 (see FIG. 23) and upper portions of the injection assembly. The first and second sections of chamber 172 are delineated by a shoulder 175 against which the dose control piece 490 bears due to force provided by a retraction spring 601 (see FIG. 24) mounted in the injector extension 303 forming part of the torsional assembly 300.

First chamber 172 still further includes a third section 177 which is used to allow space to facilitate the reception of a portion of the torsion assembly.

Second Chamber

The second chamber 272 (FIG. 29) also has several different sections which are used in the assembly and operation of the injection apparatus. There is an upper driver section 281 which receives the second driver 231 therein when the driver is in a retracted position. The driver section 281 ends at shoulder 282. Shoulder 282 is used to retain the syringe assembly there-against after the torsional assembly has been turned to the second position and the dose control has been left behind in its original position inside the first chamber.

The third section 283 is defined by a shoulder 284 which holds the injection assembly at a longitudinal position for rotation into alignment with the third rotational position for the storage of the used injection assembly after the second dose is administered.

Third Chamber

A third chamber 372 is shown most clearly in FIG. 35. This is the chamber into which portions of the used injection assembly extend after the injection assembly has been used and it is desired to store the injection assembly in a safe and contained position within the inner body piece.

Longitudinal Guides Between Inner and Outer Body Pieces

The outer body is provided with longitudinal guide slots 118. These are advantageously provided at more than one position, such at opposing positions along each side of the outer body. The slots 118 receive tangs 380 which are flexibly mounted, such as at the upper end, to the inner body side wall and provided with flexibility by having removed portions 381 along the remaining three sides thereof (see FIG. 9).

When the injection apparatus is thrust onto the flesh of a recipient, then the tangs 380 slide within slots 118 to maintain alignment between the inner and outer body pieces while allowing relative longitudinal motion there between.

First Driver Assembly

Driver Shaft Piece

FIGS. 17, 19, 21 and 30 show the first driver 131 has a driver shaft piece 132. Driver shaft piece 132 has flexible tines with barbed extensions 133. As explained above, the driver shaft piece has center safety opening 136 (FIG. 9) which is used to receive the safety pin 161 of the first safety and keep the barbs in place bearing upon the ferrule 134 until firing occurs.

Driver Spring

Figure 16:
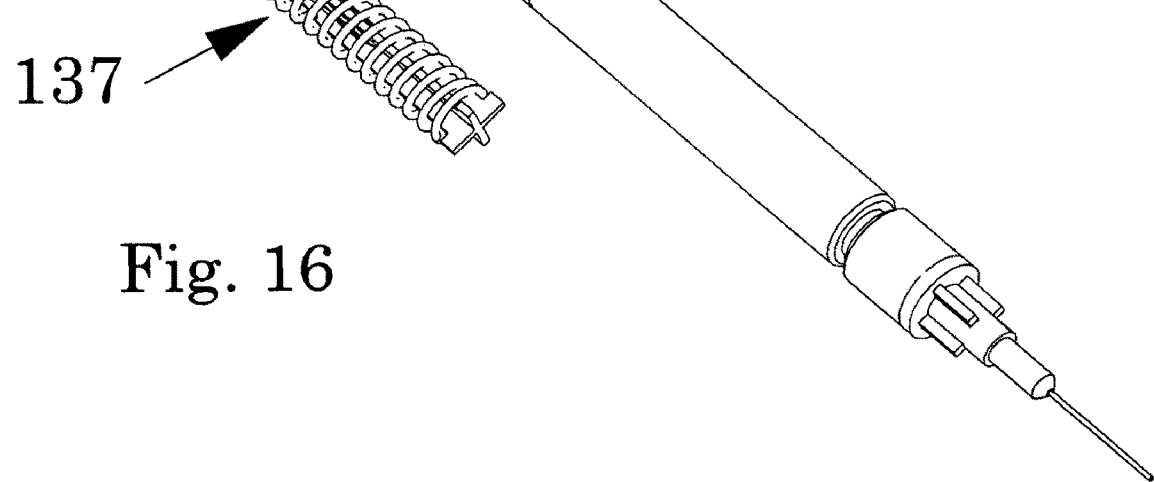
FIG. 16 is a diagrammatic perspective view of the driver spring of FIG. 15 after it has been extended.

First driver assembly 131 also includes a driver power delivery device which advantageously may store energy and release such stored energy to produce power and develop force needed to drive the injection assembly described herein. As currently preferred, such is provided in the form of a driver force delivery device, such as the driver spring 137 (FIG. 16). Other means for driving or forcing the driver shaft may also be workable or future devices may be developed which can perform this function.

Driver Safety

Figure 6:
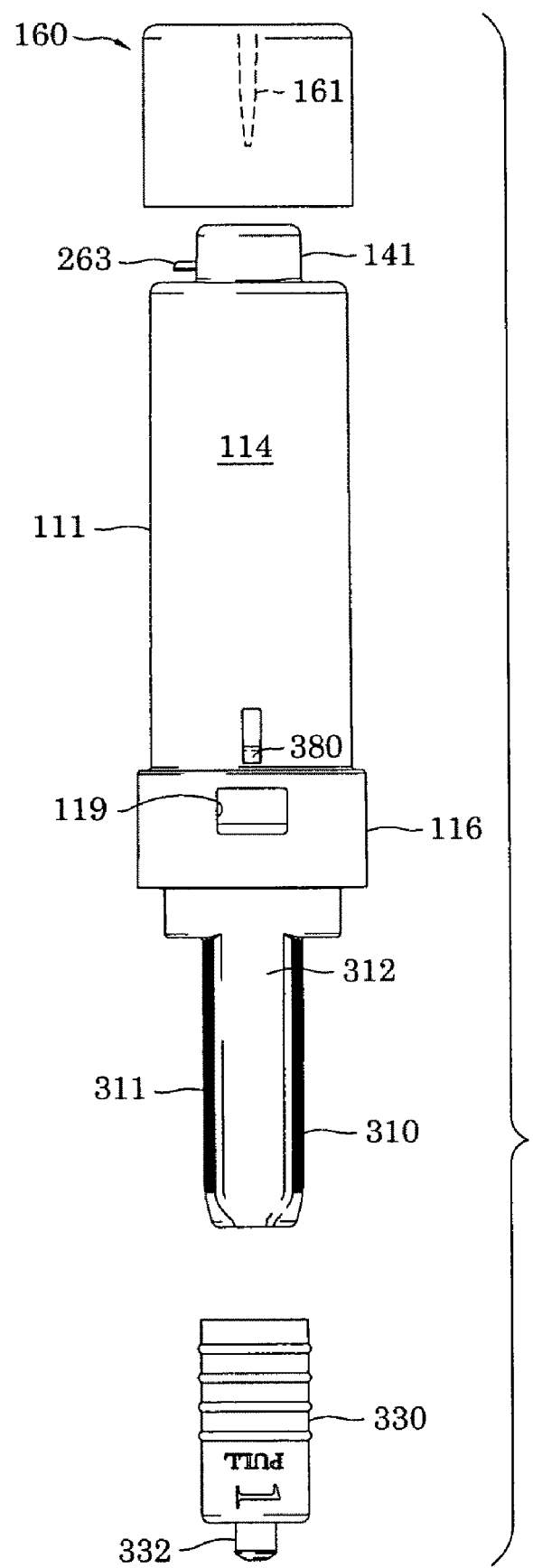
FIG. 6 is an exploded front view of the apparatus of FIG. 1 with a top cap and sheath remover shown being removed.
Figure 30:
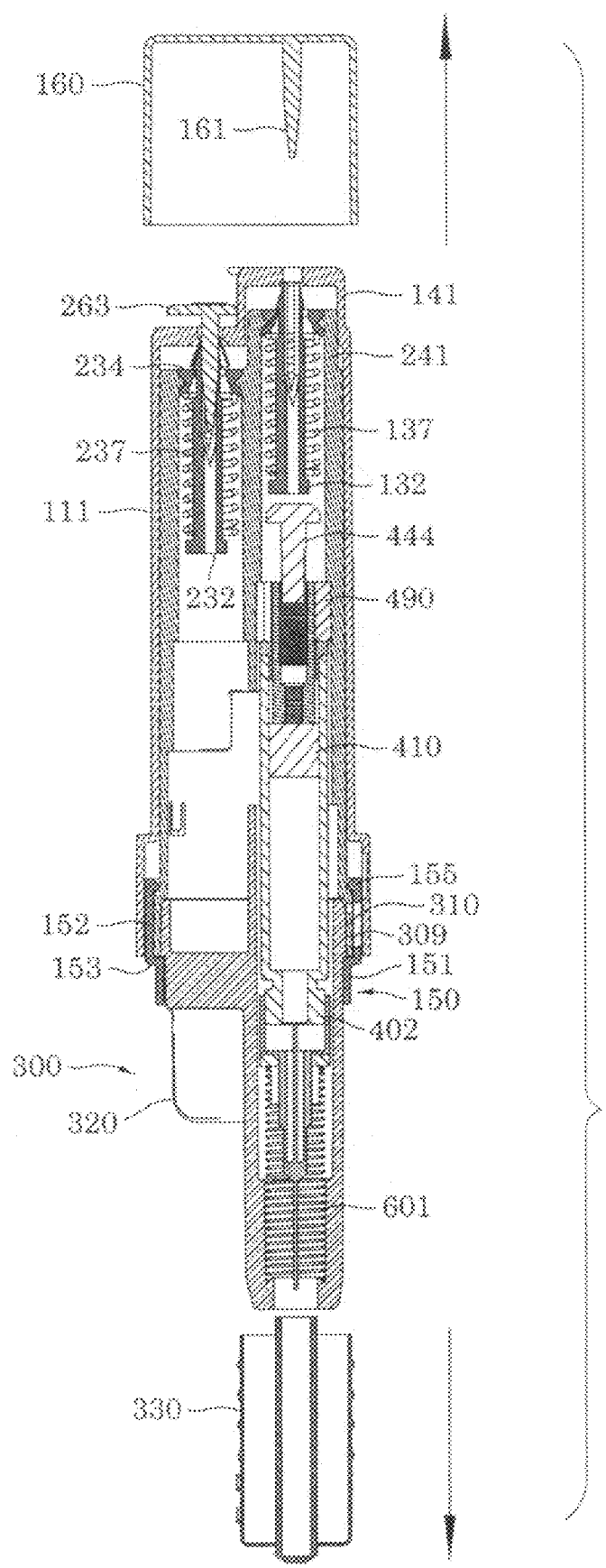
FIG. 30 shows the apparatus of FIG. 29 with the top cap being removed and the sheath remover and needle protector being removed to prepare the apparatus for use.

The first driver is retained in the safe condition by the safety pin 161 inserted into the driver shaft piece. When arming of the first driver is desired in preparing for triggering the first injection, then safety pin 161 is removed, for example by removing the safety end cap 160 as illustrated in FIGS. 6 and 30. Then the first driver is in an armed condition. In this armed condition the injection apparatus is ready to be moved in the direction of the recipient to perform the injection. This is preferably done holding the outer body in the recipient's hand, another person's hand who acts as administrator's hand, or in general in a user's hand and then moving the injector.

When the driver safety 161 is removed, then the first driver is maintained in the armed condition by the barbed extensions 133 on the driver shaft 132 which bear upon the first driver ferrule 134.

In operation the user then moves the whole injector and impacts the leg or other tissue. This causes the outer body to then slide relative to the inner body piece and the first driver is then automatically triggered and releases from the armed condition to proceed with firing. The features of the trigger will now be described.

First Driver Trigger

The first driver also preferably includes a trigger or triggering device. Although one first triggering mechanism is shown and described, others may be suitable. The preferred construction is now explained which involves the combined interaction and operation of several components.

FIG. 29 shows the barbed ends 133 of the driver shaft 132 include sloped barb outer sides. The outer edges of the barbs converge from their place of rest on the ferrule 134 toward the distal ends. After the safety is removed then the flexible tines which have the barbed ends can be made to contract inwardly. As shown, this is done by the safety aperture 146 (see FIG. 31). The safety aperture is preferably provided with chamfer edges 197 (FIG. 31) along the inside of the safety aperture 146 to help assure the proper contraction of the distal ends of the barbed tines.

When the outer body piece moves downward in FIG. 30, it causes the barbed pieces to be contacted by the safety aperture which contracts the unsafetied tines inwardly. Thus, the driver shaft 132 is now freed to move downwardly with the barbs passing through the opening in ferrule 134. The enlarged contact head of the driver piece then contacts the injection assembly contact 448 (FIG. 31) and operates the injection assembly, the construction and operation of which will be further explained elsewhere herein.

Second Driver Assembly

FIG. 29 shows the second driver-assembly 231 in sectional detail. The second driver assembly is similar to the first driver assembly. It includes the second driver shaft or center piece 232 having flexible tines with barbs 233. Also included is a second driver spring or other suitable force application and preferably energy storage and motion inducing driver power source, such as the spring 237 shown (also see FIG. 18).

The second driver piece 232 is held by a trigger retainer in the form of the ferrule 234 which is advantageously made of steel or other suitable metal for bearing strength against the force of the driver spring 237. The barbs 233 upon the flexible tines are held in a retaining position when the safety pin 262 (see FIG. 33) is in the safe position inserted within the safety receptacle formed by the barbed tines. Once the safety 260 is removed, then the second driver is placed in an armed but unfired condition.

The second safety is generally referred to as 260. Second safety 260 is used to control the ability to fire the second driver assembly. Second safety 260 is different from the first safety as will now be explained.

Figure 33:
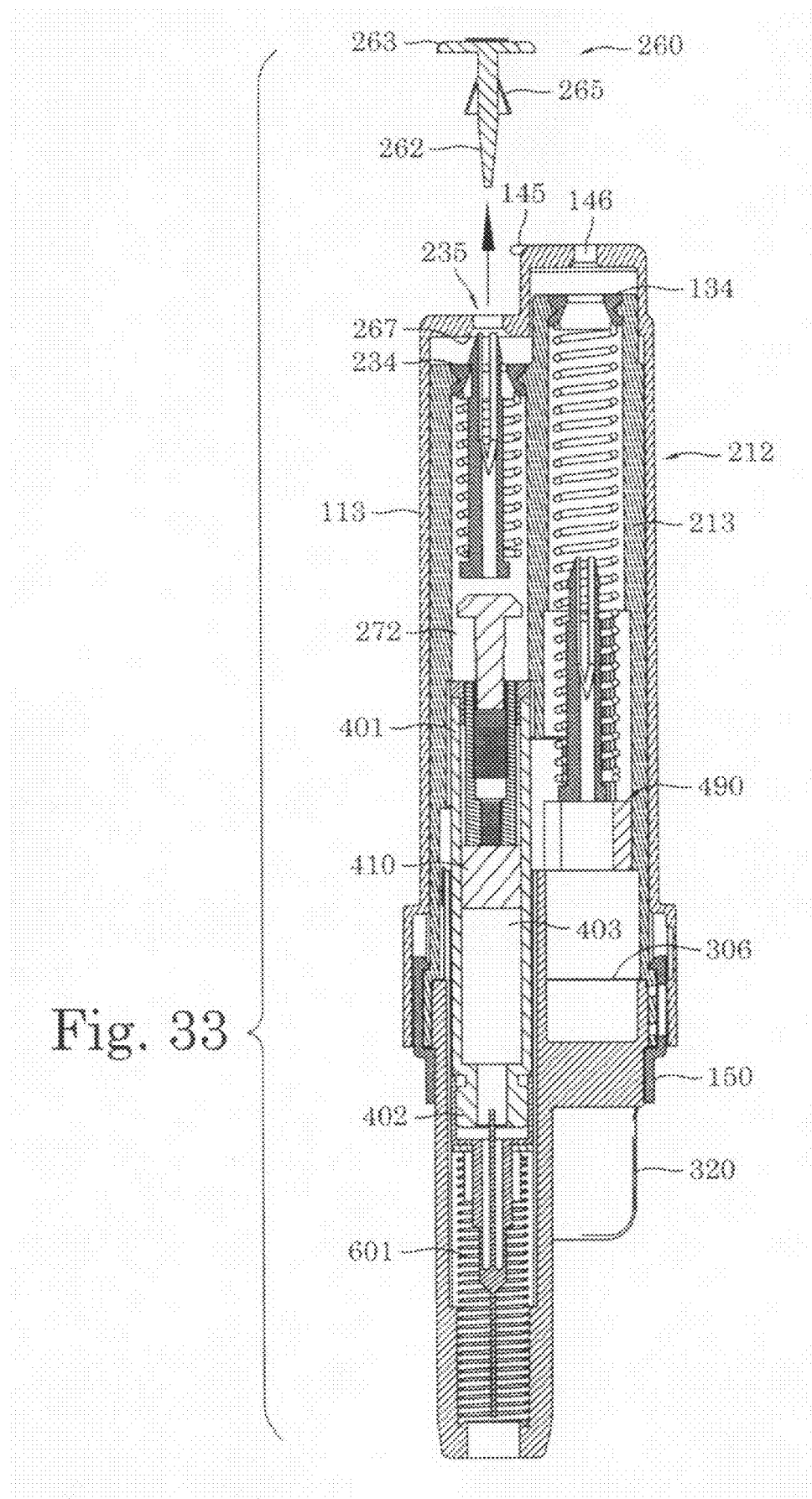
FIG. 33 is similar to FIG. 32 but shows the second safety being removed in preparation for administration of a second dose using the second driver.

The features of safety 260 are most easily seen by referring to FIG. 33. Second safety 260 includes the safety pin 262 which extends downwardly from the safety top 263. Along the pin 262 is a skirt 265. Second safety skirt 265 is flared open downwardly and is shaped to receive the barbs 233. The skirt protects against marring of the contacting firing surfaces when the first dose is administered. As the safety is withdrawn, the skirt passes through opening 235 and the safety is removed from the remaining parts of the apparatus.

Upon thrusting of the injection apparatus onto the flesh of the recipient, the flared inner surface 267 of the safety aperture moves toward and causes the barbs to contract and thus release the barbs from the ferrule 234 and fire the second stage injection. The exact angle of the surface 267 may vary from one design to another.

Injection Assembly

Medicine Ampoule

Figure 19:
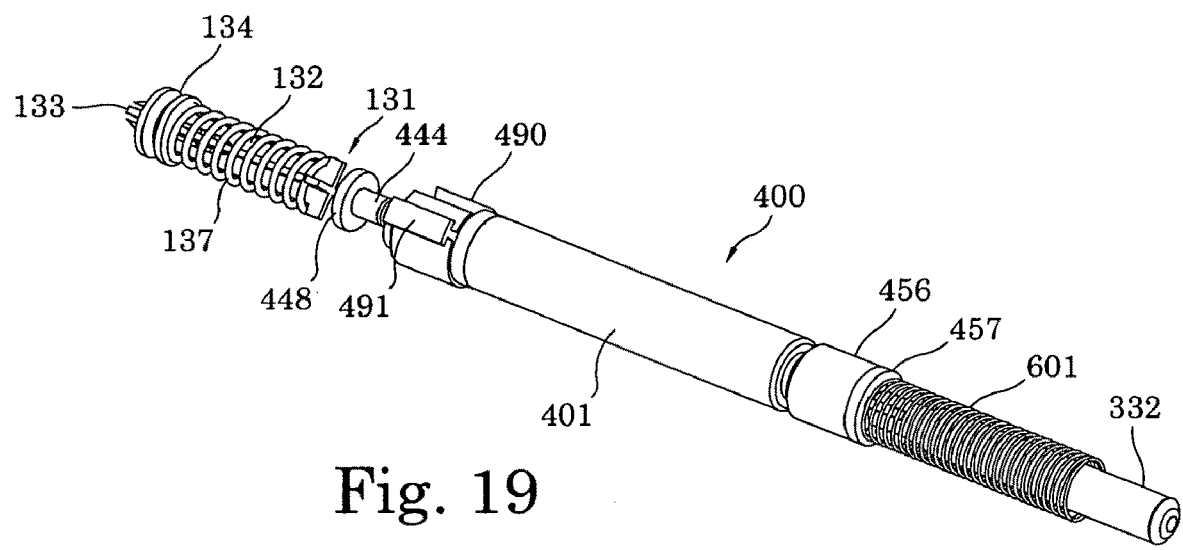
FIG. 19 is a perspective view showing a syringe assembly, driver, dose controller and a return spring surrounding the needle protector.
Figure 20:
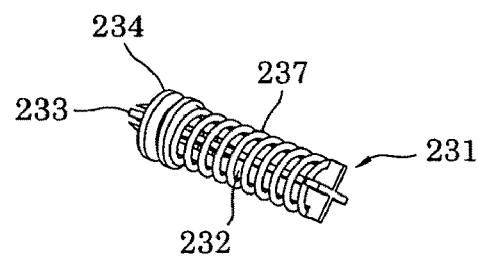
FIG. 20 is a perspective view showing the second driver spring in isolation for comparison thereto.
Figure 21:
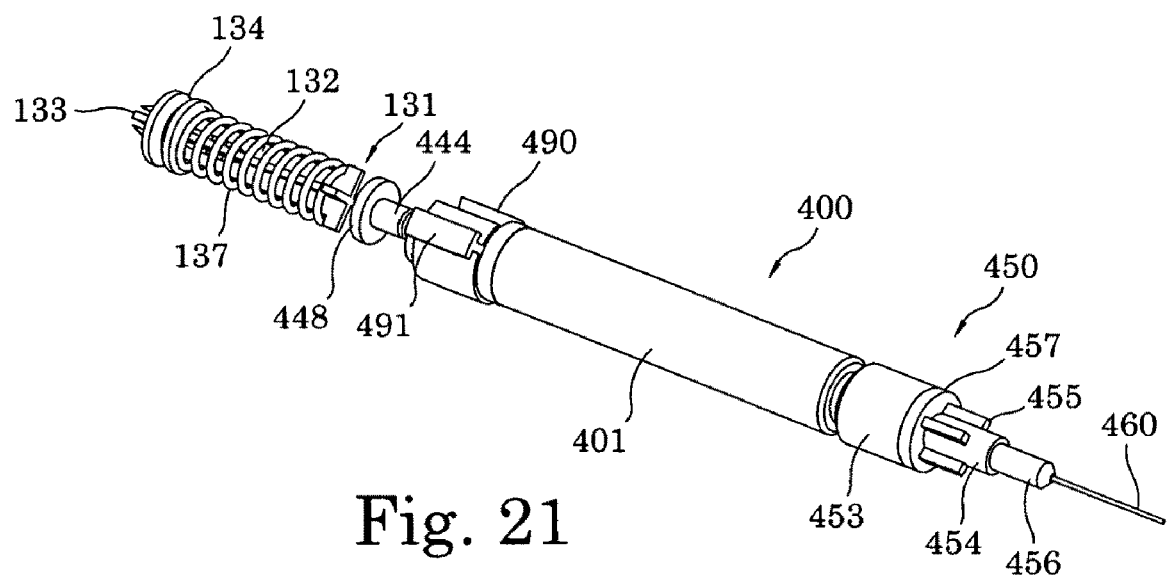
FIG. 21 is a perspective view showing the syringe assembly without the needle protector or retraction spring.
Figure 22:
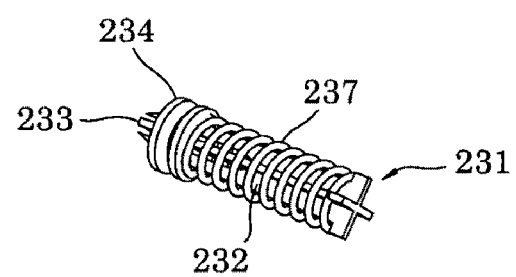
FIG. 22 is a perspective view similar to FIG. 21 with the second driver spring shown in isolation for comparison thereto.
Figure 23:
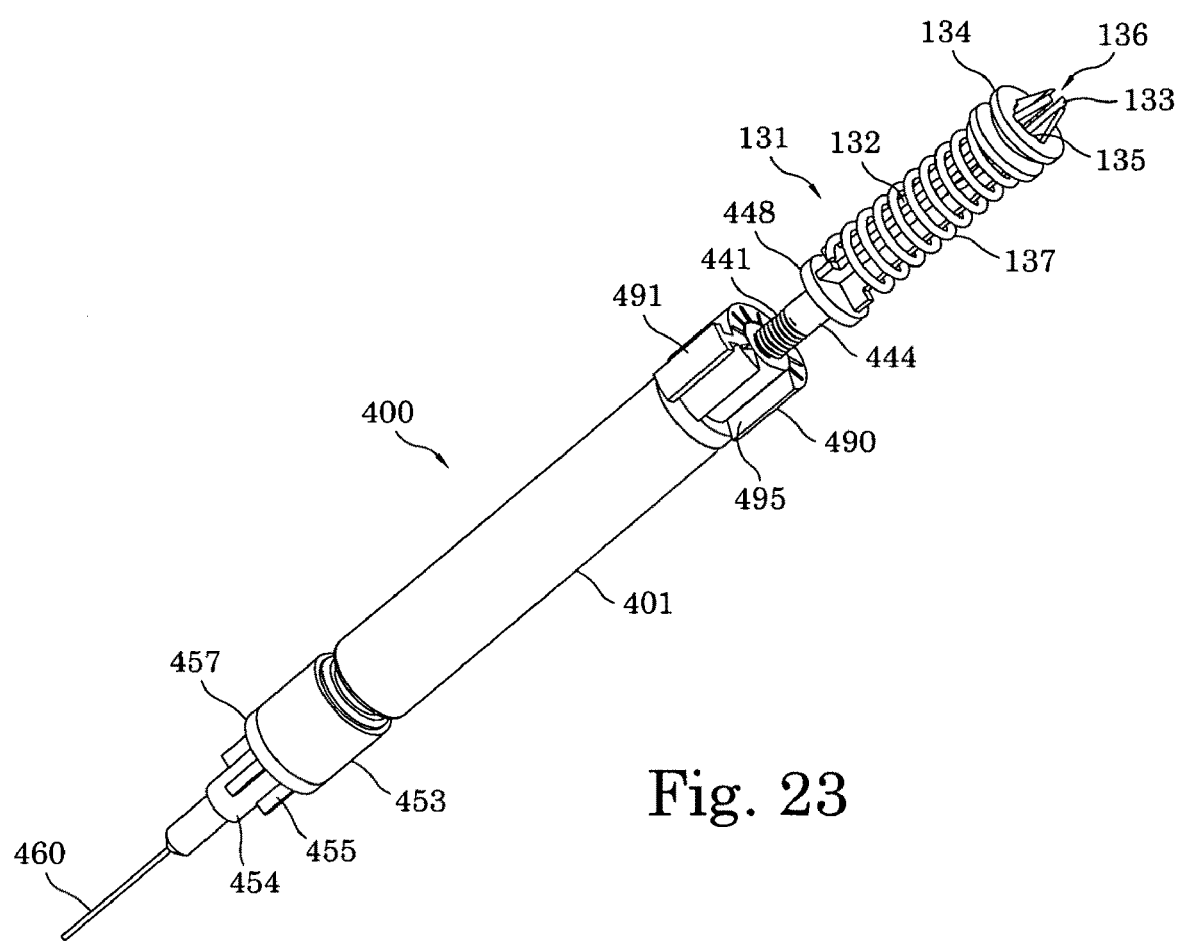
FIG. 23 is an enlarged perspective view of the syringe assembly from an upper viewing position with the driver assembly and dose controller illustrated more clearly.

FIG. 19 shows an injection assembly 400 as acted upon by a driver. The preferred injection assembly includes an enclosed and sealed ampoule 401. Ampoule 401 has a head 402 with a puncturable seal 408 (see FIG. 29). The upper end of ampoule 401 has a plunger assembly as further described below. The ampoule may be made of various materials suitable for the medicine involved, such as glass or other commonly available ampoules or ones hereafter developed.

Needle Module

The injection assembly also preferably includes a needle. As shown, the needle is a double needle assembly 450 as detailed in FIG. 29. Double needle assembly 450 has a receiver 451 for receiving the head of the ampoule when force is applied. The receiver 451 has a wall section 453. An ampoule needle 452 extends toward the ampoule and is used to penetrate the ampoule seal 408 when the ampoule is forced into the receiver, such as by the first stage driver.

The double needle assembly is also shown in greater detail in FIG. 29 and other Figures. The receiver is connected to a tubular section 454 through which extends part of the ampoule needle. The upper section of the tubular section is advantageously provided with spring guides 455.

The lower portion of the tubular section diminishes in diameter and comes together at a hub 456. Although for illustration purposes the small passageways through which medicine flows are not specifically shown, they are present to allow medicine to flow through the ampoule needle 452 through the hub 456 and out of the digital end of injection needle 460. The medicine is then dispensed or injected into the tissue of the recipient at a desired depth depending upon the medicine involved.

Plunger Assembly

The plunger assembly includes not only the plunger proper 410, but a plunger connection piece 421. Piece 421 preferably is threaded externally and is screwed into a connection barrel 420 having complementary threads for receiving piece 421. Other constructions are possible depending on the ampoule utilized; for example, the plunger could have a recess with a pressed in connecting piece.

Injection Assembly Length Adjuster

Plunger connection piece 421 also has an upper section 431 which is also preferably provided with internal threads 432 to receive a threaded shaft 441 of the plunger contact 444. Contact 444 preferably has an enlarged head 448 against which the driver contacts and bears when fired.

The contact 444 is adjustable using the threaded shaft which can be turned into the plunger connection piece to adjust the length of the injection assembly to a desired specified length to provide greater accuracy in dose administration.

Dose Limiter

Figure 13:
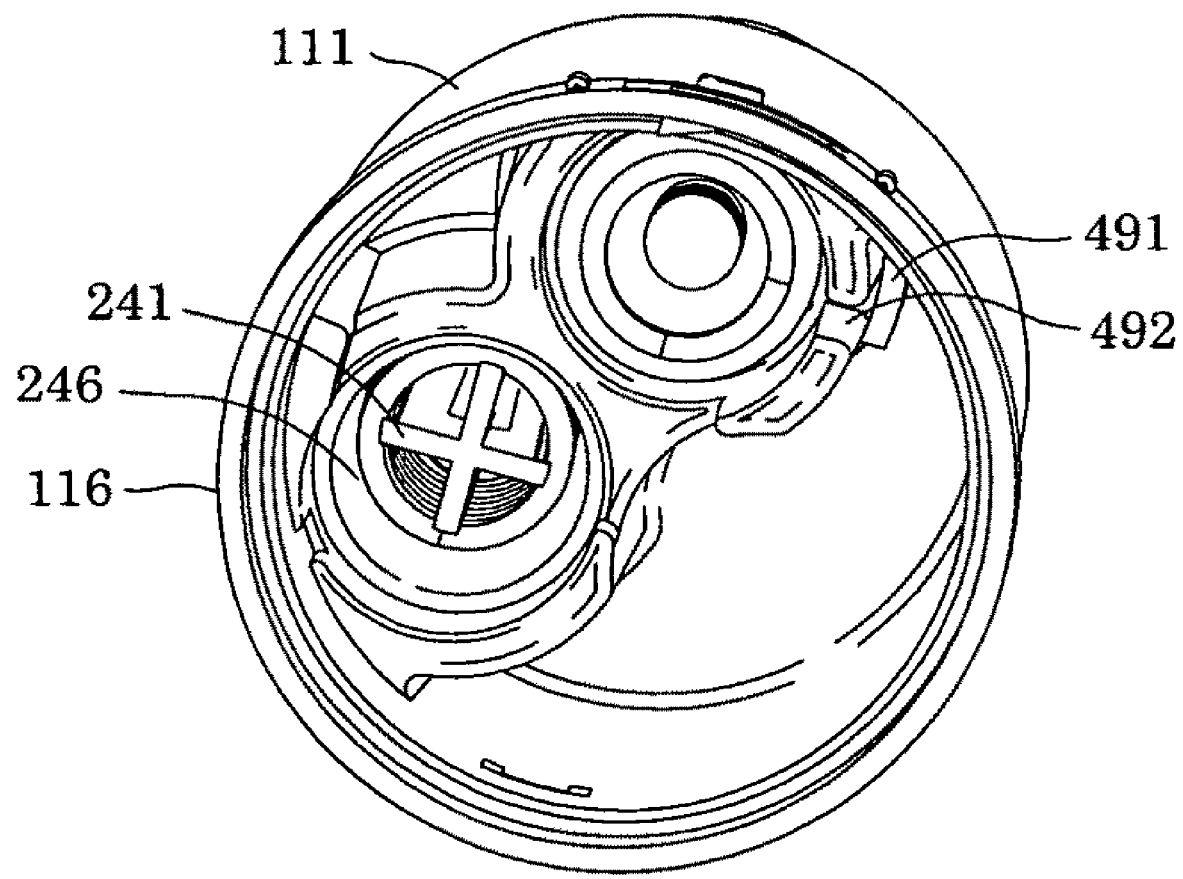
FIG. 13 is a perspective view looking into the body to illustrate the chambers and other internal parts of the apparatus of FIG. 1 removed for illustrative purposes.
Figure 14:
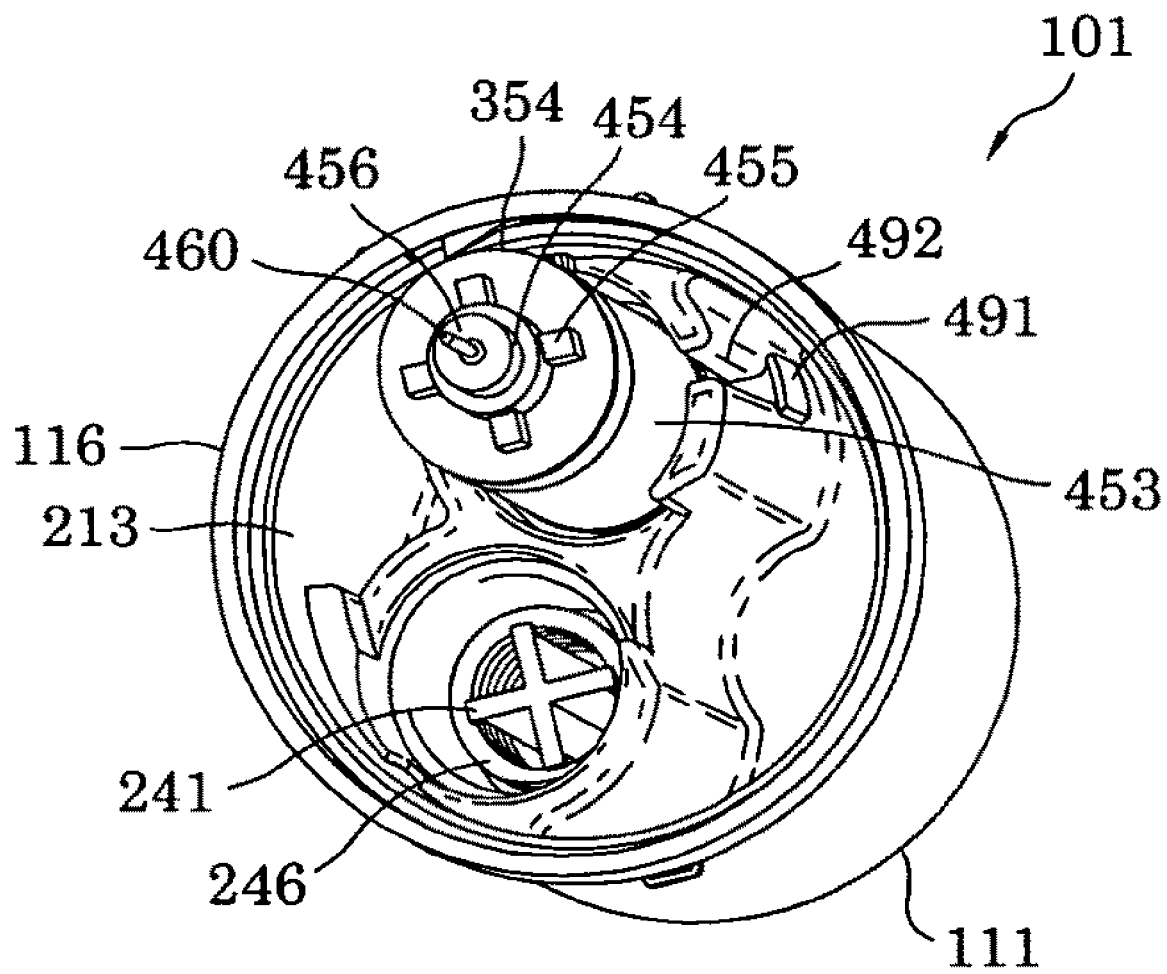
FIG. 14 is a perspective view somewhat similar to FIG. 13 with an injection assembly shown positioned therein.
Figure 15:
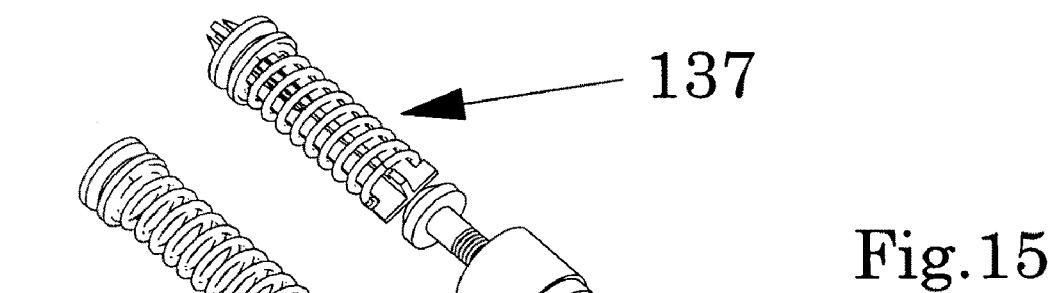
FIG. 15 is a perspective view of a driver and syringe assembly used in the apparatus of FIG. 1.

FIG. 35 and other Figures show a dose limiter or controller 490. Dose controller 490 can be seen in the transparent view of FIG. 10 and is provided with a guide extension 491 (see FIGS. 14 and 17). Guide extension 491 is received in a guide slot 492 formed into the inner body (FIGS. 13 and 14). The guide extension is provided with an enlarged head that retains the dose controller in the guide slot. Thus, after the first dose is administered then the injection assembly is stripped out of the dose controller through an opening 495 (see also FIGS. 23 and 24) in the side of the controller.

As built, dose controller 490 is advantageously provided with a series of slots or kerfs 496 (see FIG. 24) which provide added flexibility for the extraction of the injection assembly out through opening 495.

Figure 25:
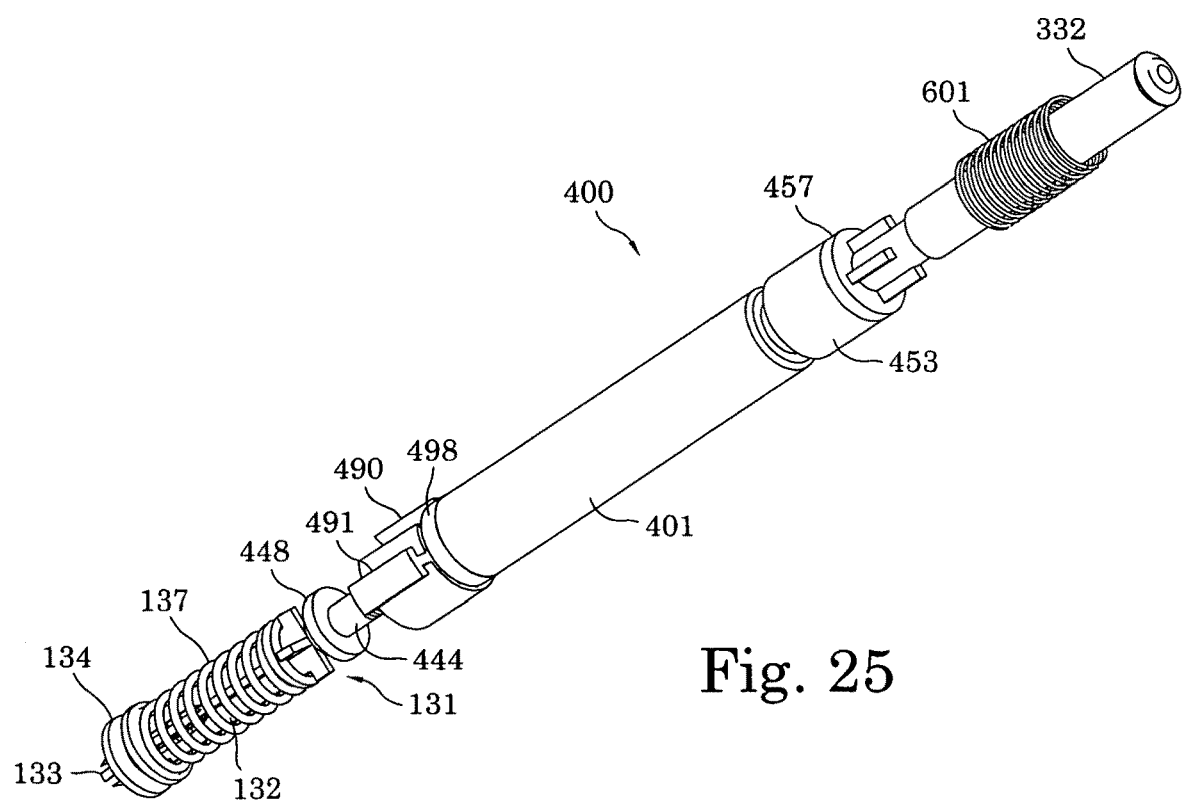
FIG. 25 is still a further perspective view of the driver, dose controller syringe assembly, needle protector and portion of the retraction spring shown from a different viewing position.

The dose controller or limiter bears upon a stress distribution bushing 498 shown in FIG. 25 and elsewhere. This distributes force applied by the drivers at both the first and second stages and laterally positioned chambers.

Torsional Assembly

Generally and Torsion Main Piece

Figure 28:
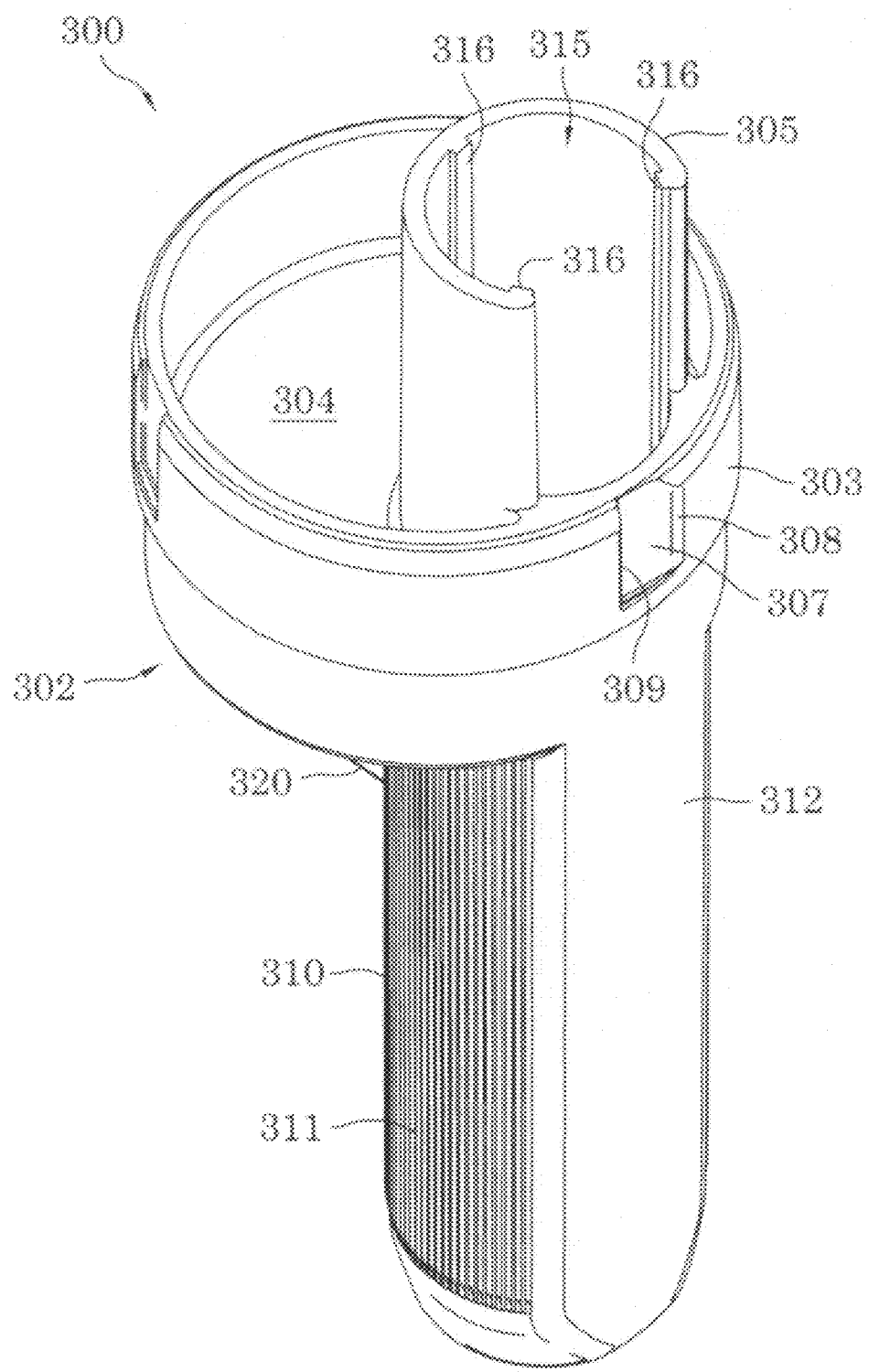
FIG. 28 is a perspective view of the torsional part in isolation.

As FIGS. 1 and 28 indicate the injection apparatus 101 includes a torsional assembly generally referred to by the reference number 300. Torsional assembly 300 includes at least one injector extension 310 which is part of a torsional main piece 302. FIG. 28 shows the torsional main piece 302 in isolation.

The torsional main piece 302 includes the injector extension 310, an insertion collar portion 303, a main piece floor section 304. The collar portion 303 extends upwardly from the floor section 304 to a top edge thereof and is received in a torsion collar receptacle or receiver 221 formed along the bottom of the inner body piece 213 (see FIG. 32).

FIG. 28 shows the torsional main piece 300 which also includes an upright extension 305 having an internal chamber 315 with injector guides 316 which guide the injector assembly longitudinally in its motion up and down at each of the three different stage positions.

Torsional Latch or Restraint

Figure 17:
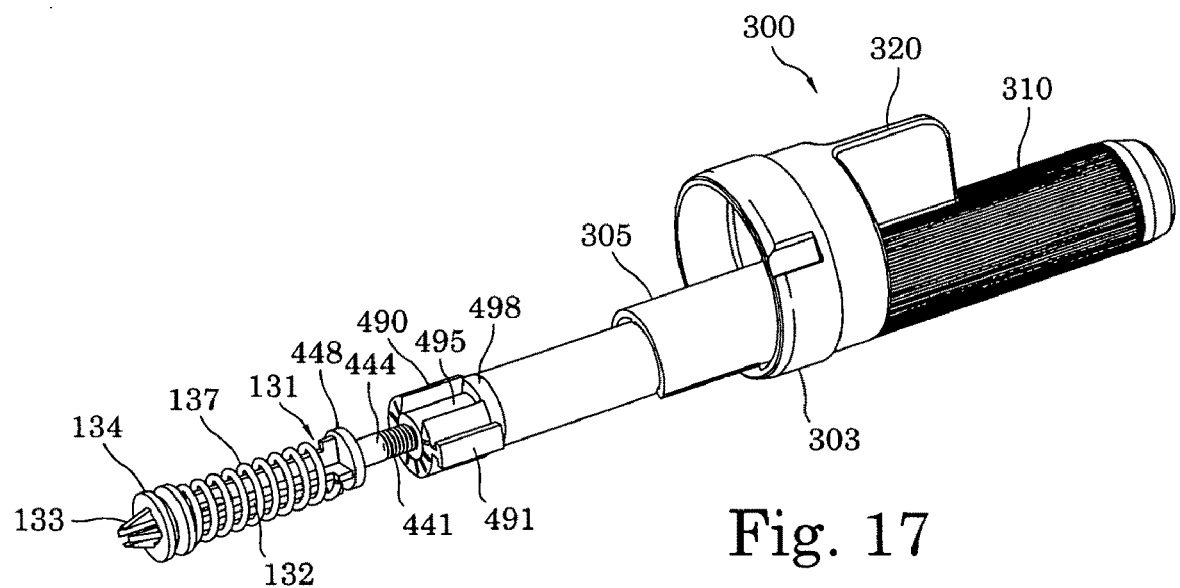
FIG. 17 is a perspective view of the driver, dose controller, syringe assembly, extending into the torsional part of the apparatus of FIG. 1.
Figure 18:
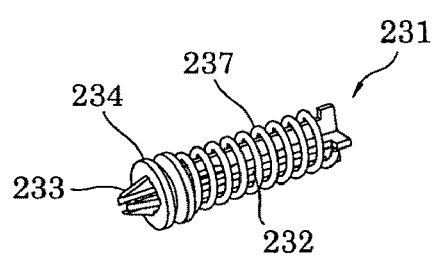
FIG. 18 is a perspective view showing the second driver spring in isolation.

FIGS. 17 and 28 show that the exterior surface of the torsional piece collar section 303 is provided with at least one torsional or angular restraint. The restraint may include a plurality of twist latch catch receptacles 307. The illustrated currently preferred twist latch catch receptacles are asymmetrically formed with a ramp portion 308 and a catch edge 309. The catch edge 309 is used to allow a latch catch 310 (see FIG. 9) to engage and stop twisting action of the torsional assembly at a desired stop position associated with the three predetermined positions of stages one, two and three of the operation of the injector apparatus. Thus the latch acts as a torsional or angular positioner to facilitate proper angular positioning of the torsional portion relative to the main body and chambers. Such can be used to provide alignment of the injection subassembly or injector with the desired chambers for driving or storage of the injector.

FIGS. 9, 29 and 30 show the torsional latch catch 310 is a more flexible piece free along three sides (as a peninsular extension) and connected to and formed as part of the inner body. The catch 310 is positioned within a twist latch catch operation window 157 formed in the side wall of the coupler 150.

Figure 10:
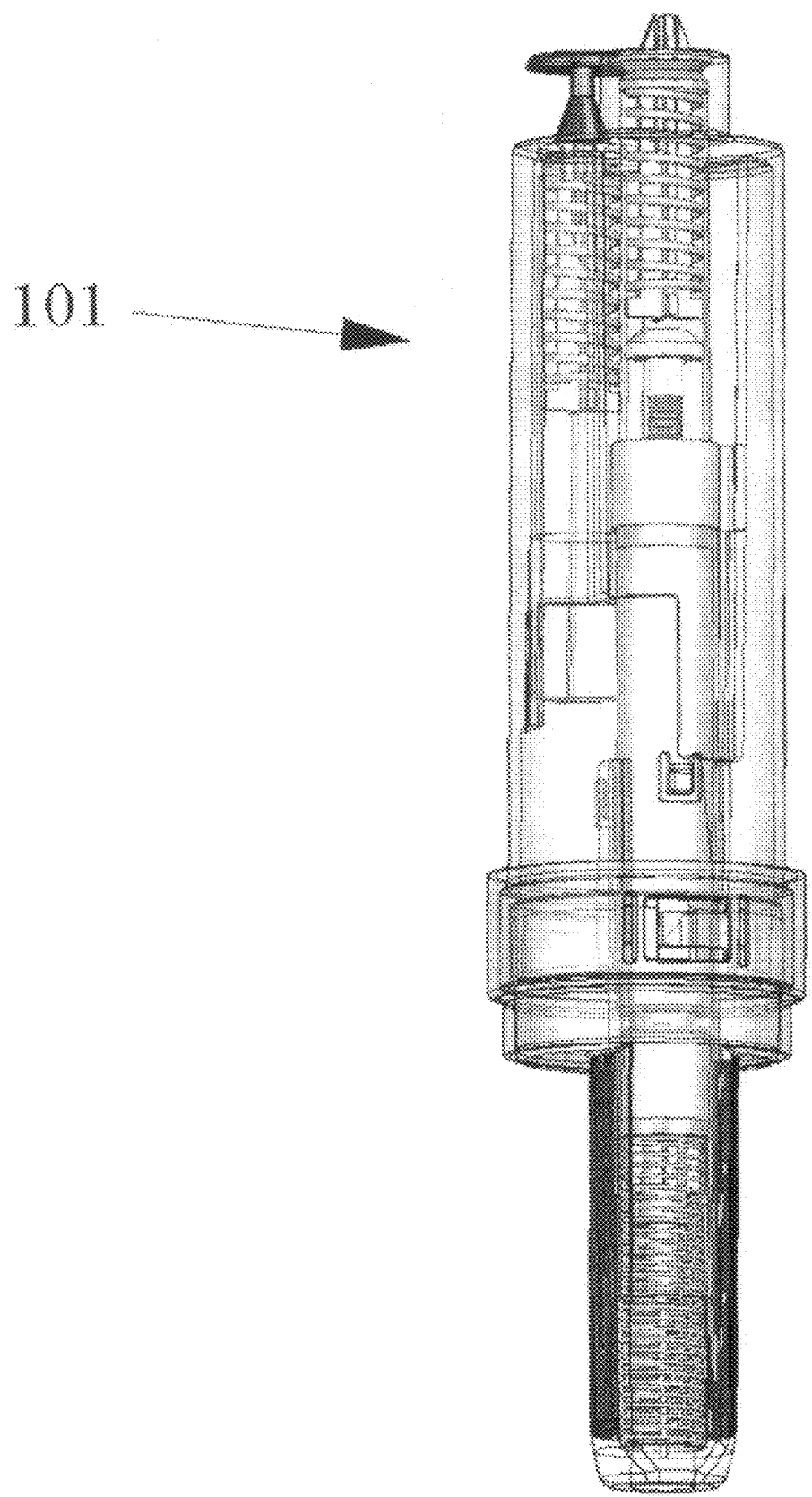
FIG. 10 is a transparent perspective view with the outer body piece removed.
Figure 11:
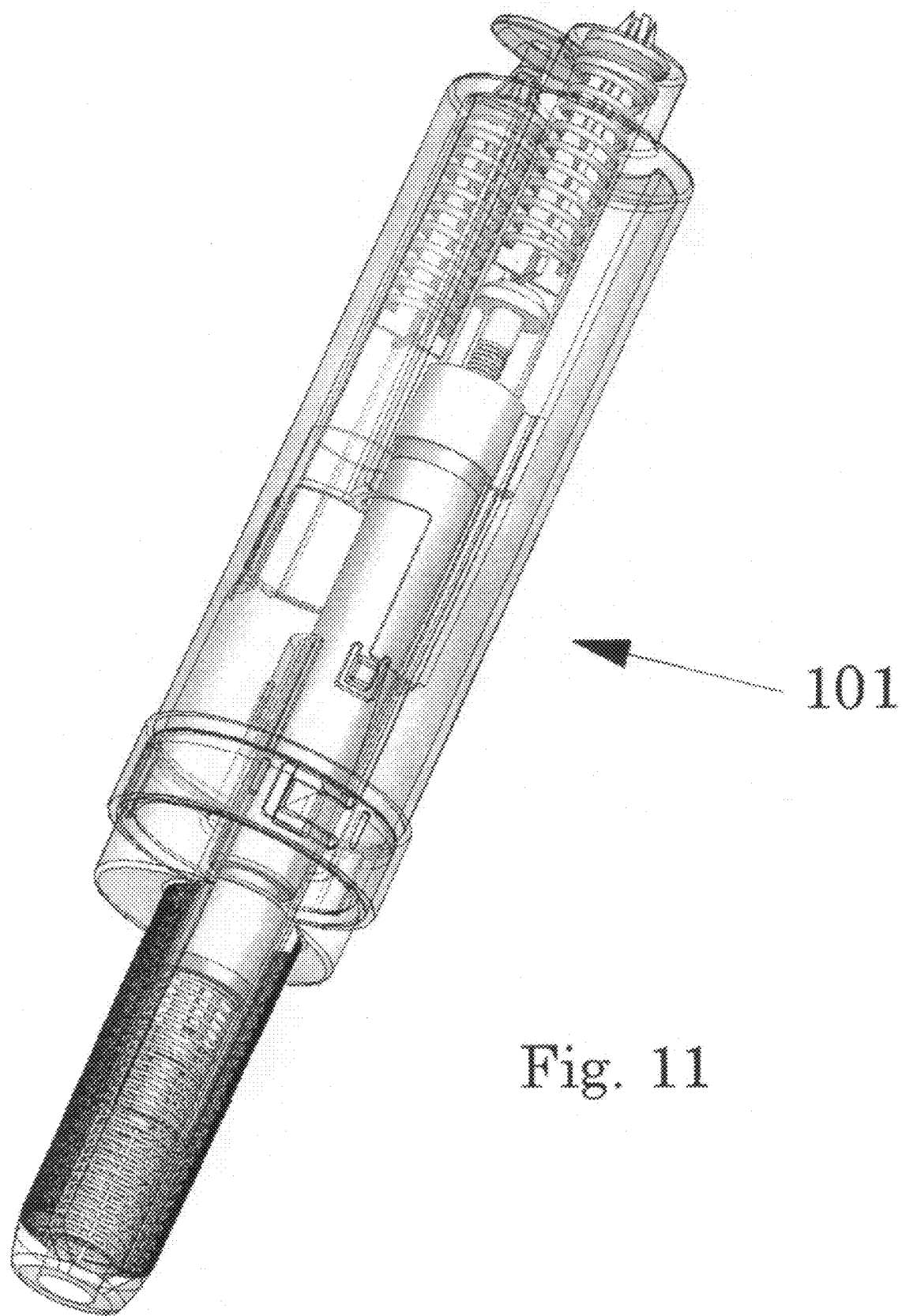
FIG. 11 is a transparent perspective view showing the apparatus of FIG. 1 with the top cap removed.

FIGS. 9 and 10 also show that torsional recesses 156 are advantageously used adjacent to window 157 and mate with projections (not easily seen in the Figs.) formed along the interior surface of the enlarged portion 116 of the outer body and further serve to mate to give further angular positional rectitude to the user of correct angular positioning of the torsional assembly as it is repositioned angularly to the three different stage positions used in injector 101.

Injector Extension or Extensions

Injector extension 310 (see FIG. 28) advantageously includes a striation section 311 which extends around part of the extension. As shown, extension 310 also includes a flat or approximately flat portion 312 also extending longitudinally along the injector extension. FIGS. 6 and 7 indicate that the striations and flat portion extend down to an extension distal end 315. As shown, distal end 315 includes a distal port 316 (see also FIG. 32).

FIG. 1 also indicates that the torsional assembly may include a torque applicator 320. Torque applicator 320 may be in the form of an extension or torque application fin 320 which extends from the injection extension 310 to the floor portion of the torsional main piece 302.

The injector extension and torque applicator 320 both aid in a user turning the torsion assembly relative to the upper body pieces.

Sheath Remover

Figure 2:
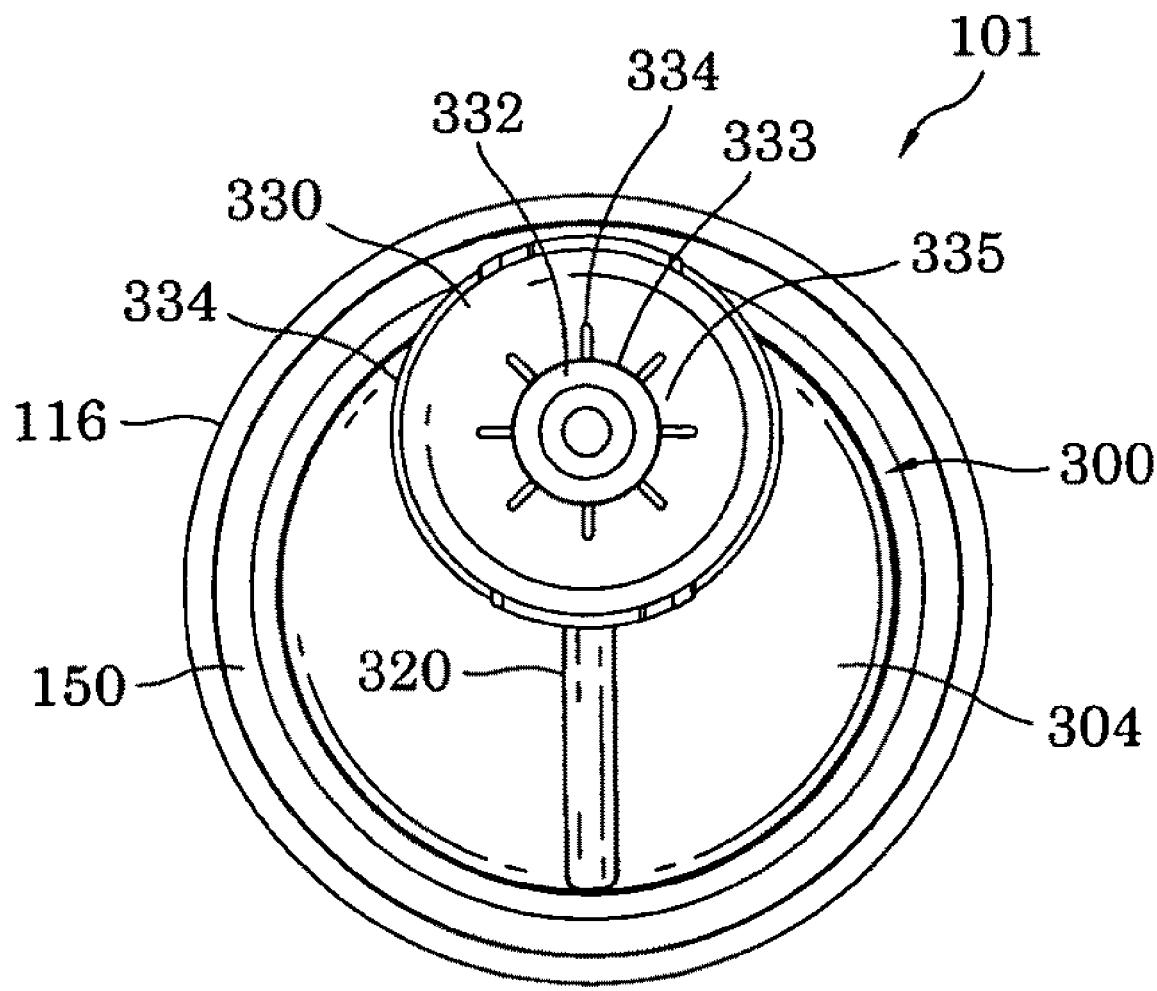
FIG. 2 is a bottom view of the embodiment of FIG. 1.
Figure 3:
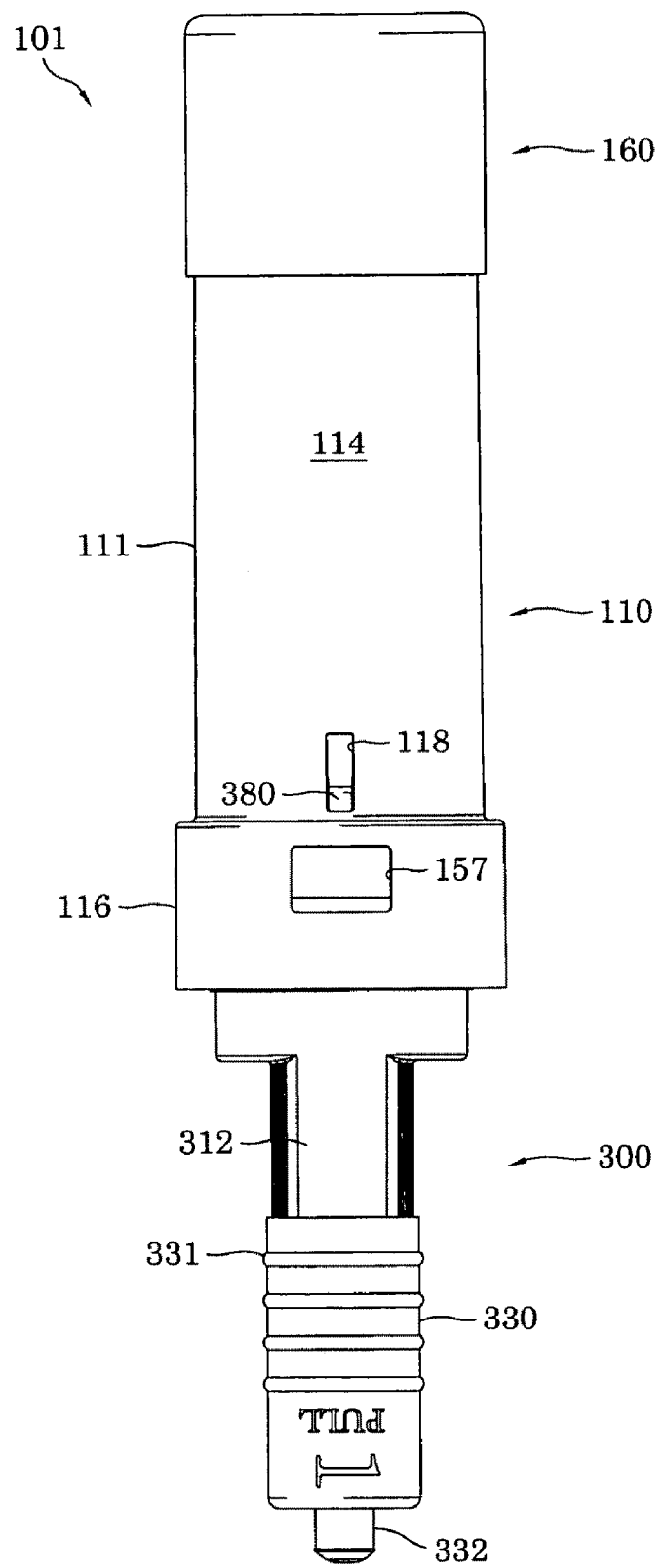
FIG. 3 is a front elevational view of the embodiment of FIG. 1.
Figure 4:
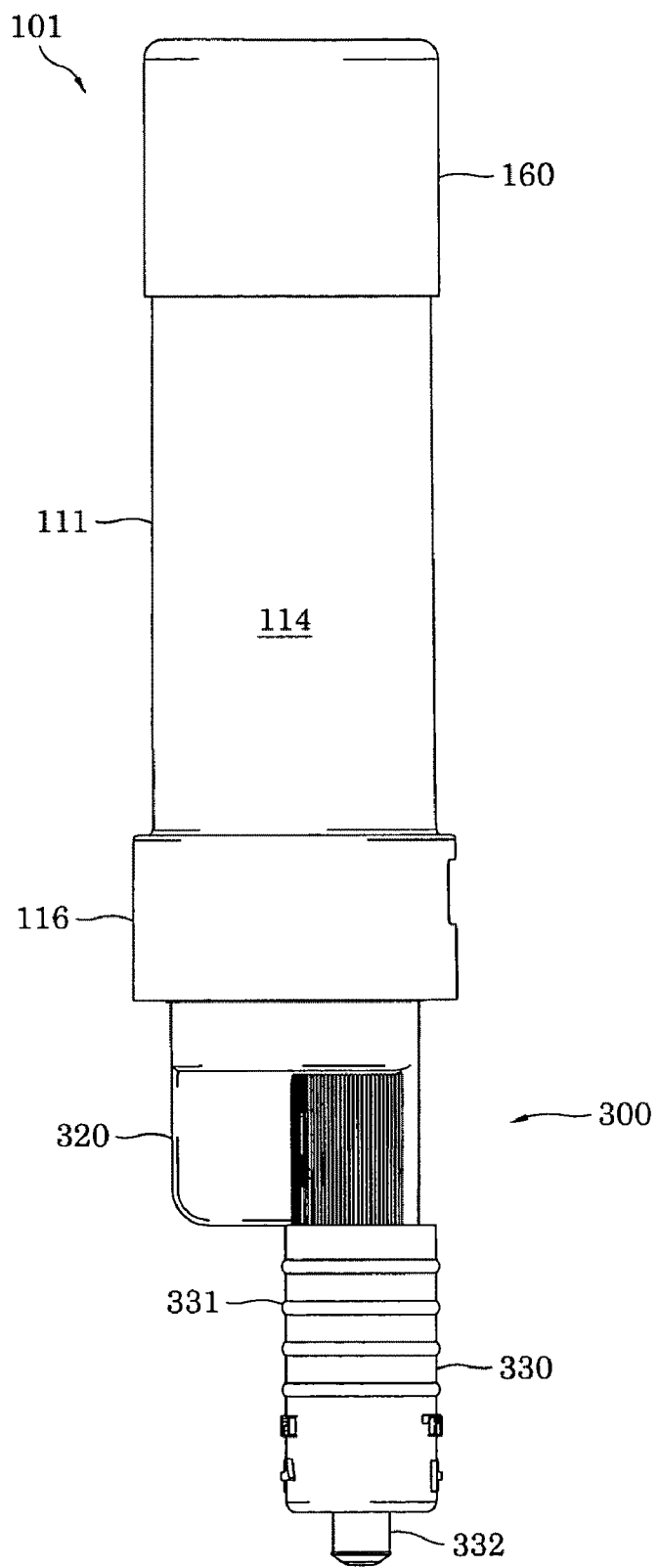
FIG. 4 is a side elevational view of the embodiment of FIG. 1.
Figure 5:
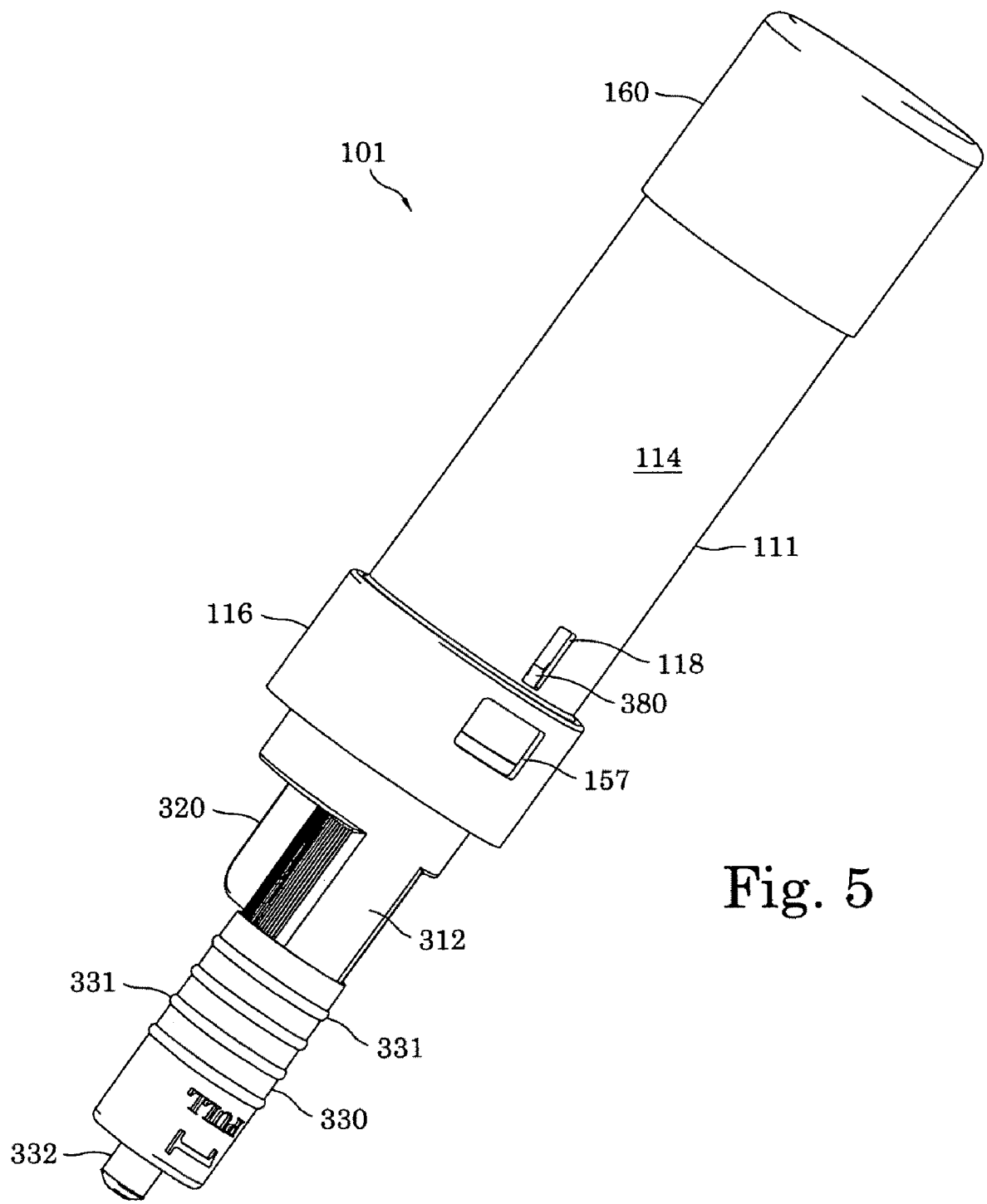
FIG. 5 is a perspective view of the apparatus of FIG. 1 from another viewing angle.

FIGS. 1 and 2 show that injector 101 preferably includes a sheath remover 330 which can be provided with gripping rings 331 which aid in removal of the cap from the injection extension 310. The sheath remover is advantageously provided with a needle sheath aperture 333. Sheath aperture 333 receives the needle sheath 332. The sheath aperture may be provided with flexing segments 335 using slots 334.

Injection Needle Sheath

FIG. 25 shows selected components of the apparatus 101 for clarity of presentation in a pictorial view which helps to easily illustrate such selected components. FIG. 25 shows the injection needle sheath 332. Sheath 332 is used to cover the injection needle 460 to maintain sterility or a sufficiently hygienic condition prior to use of the apparatus. Sheath 332 also helps to more generally protect needle 460 which forms part of the double needle assembly 450.

The injection needle sheath is adapted to be received over the injection needle in a manner which is preferably supported in such a way that the sheath does not contact the needle. This is best illustrated in the sectional view of FIG. 29. The sheath has a proximate end that is sized and otherwise adapted to slide over the portion 454 of the injection needle assembly.

Injector Retractor or Return Spring

The injection assembly has a retractor which is a suitable retraction biasing or other suitable mechanism to return or apply force in opposition to the at least one driver. As shown, the retractor is directed toward retraction of the injection assembly. The preferred retractor is in the form of a compression spring 601 (FIG. 19). The biasing provided by retractor spring 601 is in the illustrated version in the form of spring 601 applying force upon the injection assembly. More specifically, this is advantageously done by applying force between the injection extension against the injection assembly, such as against the needle assembly 450.

The retractor is advantageously made by applying force directly or indirectly to the injection assembly. The construction shown uses spring 601 which applies force to the injection assembly at the needle assembly 450, such as at the hub thereof. This is preferably done indirectly in some constructions to equalize the forces about the hub and minimize any risk there might be of effects upon the ampoule or needle assembly. As shown, this is done using a cushion in the form of a cushion washer 457. In the preferred construction the cushion is a washer 457 made of nylon, suitable elastomeric polymers, or other suitable materials now known or hereafter developed.

The opposing end of the retractor spring 601 is supported upon a ledge 458 (see FIG. 29) formed into or otherwise provided in or against the injection extension, such as near the distal end thereof. Other suitable ways to mount the retractor and any retractor spring included therein may be possible although the current design is currently preferred.

During operation the retractor, such as spring 601, compresses as the drivers move the injection assembly into extended positions, such as penetrating positions of the injection needle 460. This resists the driver force increasingly as the injection needle 460 is driven into the recipient's flesh. This may help to slow the injection assembly and reduce any shock that might occur dependent upon the relative strengths of the respective retractor and driver springs with some possible constructions, and as the spring 601 compresses it can or may provide some of the penetration depth control desired from an injection.

Torque Application Features

The injection apparatus is advantageously provided with features which may facilitate twisting of the upper assembly relative to the torsional assembly. A variety of different things may be used to facilitate the twisting or turning. As shown, the apparatus is provided with a torque application part 320 which can facilitate fingers, thumb or other hand digit to provide or allow manipulation to help turn the upper assembly relative to the lower or torsional assembly.

Also included is or are one or more texturized surface or surfaces upon the injection extension. As shown, this is implemented in the form of striations. Flat portion 312 may also in some instances be of help to a particular user in turning or otherwise twisting the upper and lower assemblies relative to one another.

Penetration Controller

Apparatus 101 or other injection apparatuses according to the invention are advantageously provided with one or more features which serve or help provide reliable penetration control. In the preferred embodiment shown the penetration control is simply provided by the fully compressed length of the retractor spring 601, plus the included cushion washer.

Alternatively there are a variety of penetration control constructions which may be provided using various features shown and described in the incorporated by referenced patent referred at the top of this document.

These and other penetration controller constructions may be used if suitable where they are now shown or hereafter developed.

Coupling or Coupler

FIGS. 29 and 30 show a preferred coupler 150. Coupler 150 or other suitable couplings may be used to hold the torsional assembly 300 to the upper assembly. Coupler 150 is advantageously formed as an annular piece with a smaller section 151 and a larger section 152 having an adjoining shoulder 153.

The upper or interior end of coupler 150 at the larger section 152 has an annular inward locking projection 155. Locking projection or projections 155 catch over and lock over the inner body assembly 212. This couples the torsional assembly and inner body assembly.

Multiple Medicine Injections

Generally

Apparatus 101 includes a single injection extension and a single injection syringe. It is alternatively possible to use multiple injection syringes and multiple injection extensions. This may increase the size of the apparatus depending upon the volume of medicament being injected. It also may provide the ability for more capacity of one type of medicine. Still further it may provide the ability to use plural ampoules or syringes containing different medications.

Although such multiple medicine variants are possible by utilizing constructions similar to that shown herein, they are not currently preferred as the best mode. However, in the numerous different medical applications and medicaments to which apparatuses according hereto may be used, then such alternative versions may be desired.

Connection of Multiple Units for Portability

It is also possible to assemble plural apparatuses 101 into an arrangement of suitable configuration to the specific needs or desires of different situations. For example, it is possible to connect plural apparatuses using a flexible connection therebetween to allow multiple adjoined injectors to form a flexible strip which may be visualized as similar to bullets in a strip used in automatic gun cartridges, or machine gun ammunition. These types of configurations could allow the array of multiple injectors to be rigid or more preferably flexible to conform to the curvatures of a human body. For example an array containing 2 or 3 might be flexibly connected and carried adjacent to the thigh of a person carrying the injectors.

Still further the array may be made to form a circumscribing belt configuration which may be worn about the torso, ankle or other part of the body. This may in particular be desirable in military or other situations where a person needs to carry greater doses of medicine (such as a military medic) or may be venturing into remote terrain and greater variety of medicines are desired for proper or desired use to provide more injections and/or more injections of multiple different medicines.

Methods and Manners of Using and Operating

Overview of Summary of Operation

A summary will now be given as to the operation of the preferred apparatus detailed herein. The apparatus is produced and stored in preparation for use in injecting a desired medicine, for example epinephrine and others.

The apparatus is prepared for injection by first removing the injection end cap piece that is principally used to remove the needle sheath and also provides some degree of protection to the injection extension. Once the injection end cap is removed, then the opposite cap is removed from the upper end. The cap as shown contains the safety for the first stage and thus removal of the upper or safety end cap arms the first stage for use.

To use the apparatus to provide the first dose, the user simply moves the apparatus toward the desired injection location upon the recipient. For example self administration would involve in many cases the movement by hand of the injection apparatus toward the leg of a user, such as in a somewhat swinging action. The outer body part is held in the hand and the injection extension strikes the leg. The inertia of the user's hand and injection device causes the outer body piece to continue to move after the injection extension contacts the user and is effectively stopped. The outer body continues downward and moves relative to the inner body and causes the triggering of the first stage driver. This releases the driver, such as the driver spring. The driver spring then forces the driver contact into engagement with the injection assembly and pushes the plunger and injection assembly toward the recipient in an injection movement process.

The injection movement process extends the injection assembly from the apparatus and drives the injection needle into the user's flesh. Continued force pushes the plunger and dispenses the medicine through the injection needle into flesh. The amount dispensed is preferably controlled by the dose limiter so that about half or other appropriate amount of the medicine is dispensed into the flesh.

The return spring or other retractor is compressed during the injection and may be used in combination with the shock absorbing washer to limit penetration depth. After the dispensing of the medicine then the injection assembly stays in an extended position until the torsional assembly is rotated relative to the remaining parts of the injector. When the next stage position is achieved then retraction back up into the apparatus can occur and the injection needle is then preferably fully hidden. Features within the inner body keep the injection assembly extended during repositioning between the angular positions for the various stages.

The user then holds the upper part and turns the lower part in a twisting action after releasing the torsional latch. The lower portion comes to a second position where the injection assembly is aligned with a second driver in the embodiment illustrated. The torsional movement removes the dose limiter and thus prepares the injection assembly for a second stage driver to dispense another portion of the medicine by allowing the second driver to push the plunger further into the ampoule.

The second driver is armed by removing the second safety. A similar action as indicated above is done to administer the second dose as may be desired or needed. The injection assembly and injection needle stay in an extended position until the rotary or torsional part is rotated to the next stage position or sufficiently close to allow retraction by the return spring.

After the second and any subsequent doses for which the injection apparatus is designed are used, then the user can again torque the lower part relative to the upper part and place the injection assembly into storage position if the apparatus is so designed. The injection assembly is a "sharps" storage device which is preferably hidden and stored so that no subsequent injury can occur.

Once all doses provided or desired are administered and the injection assembly is stored in any provided storage chamber, or injections are stopped before all subsequent injections are utilized, then the apparatus has been used and can be disposed of in an appropriate manner. The ready positions of the subsequent stages may be used as storage positions when remaining injections are not used. Thus, effective storage can alternatively be used in an injection stage. Alternatively, if the injector is not fully used the injector can be moved to any storage position provided and a partially or unused injector can be positioned into the storage chamber when conditions so warrant or the user otherwise decides such is appropriate. This is preferably done after reinstallation of the injection end and safety end caps. It may also or alternatively be done utilizing an outer storage container shown in the referenced patent indicated at the top of this document.

Additional details of operation and methods will now be provided to further detail the processes summarily described above for the illustrated version of the invention.

Pre-Injection Conditions and Factors

Fully Assembled Condition

FIGS. 1 and 29 in particular show the injection apparatus in a fully assembled and unused or unfired condition. In such condition the apparatus is secured against accidental firing, needle exposure and resists in-migration of dirt or other contaminates.

Storing of Unused Apparatus

The injector apparatus may be kept for use by storing for significant periods of time. The storage duration is principally dependent upon the life of the medication stored in the ampoule. This is also in some cases affected by the ambient conditions during storage, for example the ambient temperature and humidity are one or more factors in some situations. Since the construction shown uses a sealed ampoule and the needle assembly does not disturb the ampoule until firing then shelf life is improved.

Alternatively, it is possible to use a syringe assembly that is preformed and uses a single needle, but such is not currently preferred.

Still further a storage of the apparatus may further be enhanced by utilization of an outer storage container, such as shown in the incorporation by reference patent indicated at the top of this document.

Sheath Removal

In a preferred manner of use and methods according to some preferred versions of use, the first step is removing the sheath that covers the injection needle from the distal end of the injection extension. This is done by pulling the sheath remover longitudinally away from the upper part of the apparatus. In the figures shown, this is typically downward.

Top Cap and First Driver Safety Removal

Another step in using the apparatus 101 and preparing for firing is removing the top cap. This is advantageously done by moving the cap longitudinally away from the upper part of the apparatus.

The removing of the top cap may also serve as arming the first driver. This arming of the first driver occurs as a result of withdrawing or otherwise changing the first driver, such as by removing the first safety pin. This removing of the first driver safety arms the first driver by removing the pin which maintains the flexible barbed prongs of the driver bar in outwardly extending positions. After removal of the safety pin, the prongs are capable of performing by flexing inwardly toward one another.

Firing of First Dose

Generally

FIGS. 1 and 29 show the injection apparatus 101 in the fully assembled condition prior to any action toward use. Additional views and states, conditions and positions will be described herein and reference may be made to reference numbers shown in other views in some instances without implying a return or change in such state, condition or position.

Sheath Removal

FIGS. 6 and 30 illustrate the action of removing the sheath removal cap 330 and engaged sheath 332. This is advantageously done first in the preferred embodiments of operational use. The sheath removal or de-sheathing step as in the illustrated embodiment performed simultaneously with a de-capping step which involves removal of the cap 330. Cap 330 is primarily used to remove the sheath, but also helps to provide protection of the injection extension until such cap is removed.

Although the preferred methods involve simultaneous removing of a cap 330 and sheath 332, it may in some versions be desirable to have such steps be done independently. Still further there may be an outer protective cap or casing (not shown) which can be removed.

Arming of First Driver

FIG. 30 shows the action of arming the first driver by removing the safety cap 160 and extracting the safety pin 161 from the safety aperture and from between the first driver barbed tines. This action of arming the driver allows the triggering next described.

Triggering and Release of First Driver

Firing of the first stage occurs by triggering the first driver. In the construction shown, this triggering action serves to allow a releasing of the first driver piece after the safety pin is removed as indicated above. In the preferred embodiments, this is performed by contracting the flexible tines. As shown, this is done by forcing the tines using a tapering relationship between the tines outer surface and the safety aperture or other suitable contracting and/or otherwise releasing of the driver trigger. As shown, this is done by allowing the barbs on the tines to act by passing through the driver ferrule aperture.

After the triggering is effected by moving the injector and impacting or otherwise forcing the relative longitudinal movement between the inner and outer body pieces, or otherwise releasing or triggering the driver, the driver acts by forcing the driver impact or contact. This contacting of the driver against the injection assembly is shown in the illustrations by forcing the head of the driver center piece against the enlarged head of the plunger assembly or otherwise pushing or forcing the plunger assembly or more simply put by forcing the plunger. This forcing causes the plunger to begin moving. Such moving in turn causes the injection assembly to begin movement until stopped by the contracted stacked retraction spring and impact absorbing piece, such as in the form of the illustrated shock absorbing washer shape. This begins pressuring the medicine by displacing the plunger or other feature of the medicine container to perform such displacing.

Firing provides for dispensing medicine through the needle assembly. The dispensing also preferably includes discharging of the medicine from the injection needle. However, in the preferred embodiment shown, the dispensing is substantially performed during and/or after the injecting of the injection needle. This may be dependent upon the relative designed strengths of the retraction and driver springs or a particular embodiment. It may further be dependent upon other processes, such as some of the processes described or indicated further below or elsewhere in this document. Firing also acts by moving the injection assembly.

Initial Movement of First Driver

In the embodiments shown, after the driver starts moving it makes contact with the plunger head. Then the force applied starts moving the injection assembly. The moving is as shown longitudinal moving which is also a sliding action within the first chamber. Other manners of performing these actions may also be suitable.

Formation of Syringe Injector Assembly

In the current preferred methods the first stage firing not only performs the ultimate functions of inserting the injection needle and dispensing medicine, but additionally includes forming an injection assembly. The injection assembly is in the preferred form shown an injection assembly syringe. The injection syringe has the needle assembly and ampoule conjoined into fluid transmitting relationship therewith.

The forming of the injection assembly is further advantageously provided so as to effect a puncturing of the ampoule head seal. This puncturing or other de-sealing action provides for allows the communicating of fluid into the needle assembly.

The syringe assembly forming also includes some moving of the plunger depending upon engineering specifics of a particular design. In some preferred versions the dispensing of medicine is typically not desired in any substantial amount prior to insertion, but may be something which occurs or which is desired in some circumstances to perform results now known or hereafter recognized as desirable. This consideration is included in the design and relative strengths of the retraction and driver springs.

Insertion of Injection Needle

Figure 31:
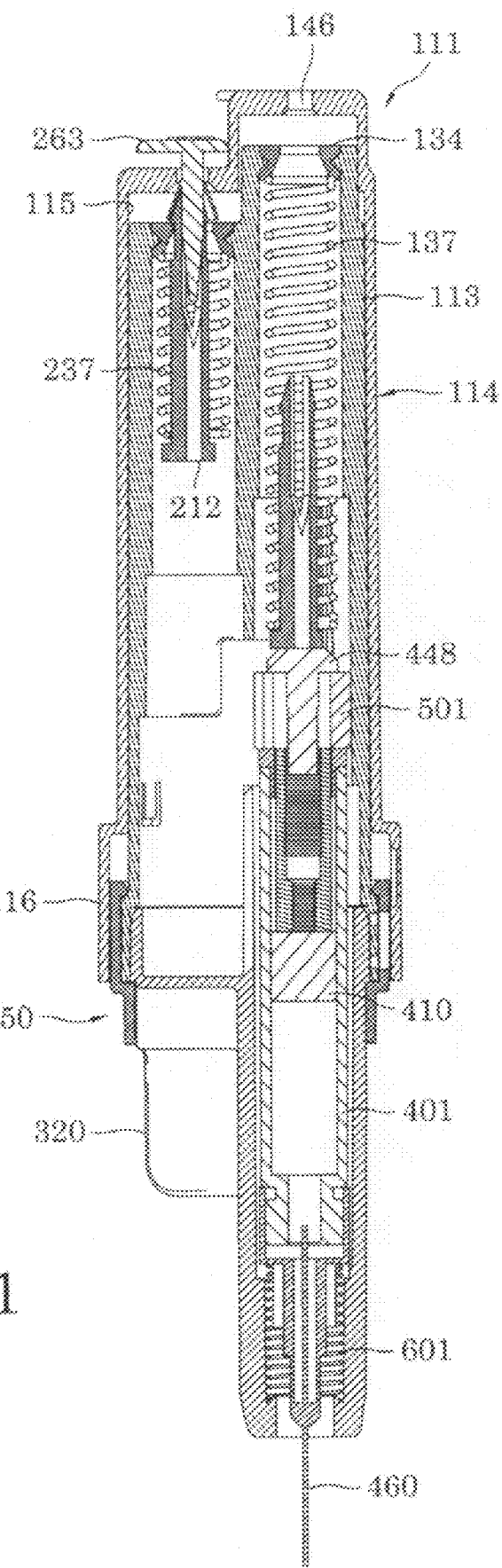
FIG. 31 shows the apparatus of FIG. 29 after the first driver has been released and the syringe assembly driven into an injecting position wherein a dose of medicine has been dispensed.

The step of inserting the injection needle is best illustrated in FIG. 31. The inserting starts when the injection needle is starting to extend sufficiently by touching the skin or other flesh of the recipient. This may be typically done after the distal end of the injection needle starts emerging from the injection extension or may in some case even begin with a compressed portion of skin or other flesh which may be compressed into the opening of the injection assembly by the forcing or impacting of the injection extension against the recipient. The extending also can be referred to as deploying the injection needle. However the dynamics of this process are dependent upon the particulars of the design, and may be affected by the recipient and the type or location of flesh being injected.

Control of Penetration Depth

In many instances the penetration depth of the discharge of the injection needle is desired at a particular depth. This may be for purposes associated with the appropriate tissue being treated, the medicine being used, the dosing of medicine or for other reasons.

In the embodiments illustrated in this document the controlling of penetration depth is advantageously performed by the compressing of the compression spring 601. The penetration depth is in the preferred form the stacked height which includes the height of the cushioning washer 457.

The patent incorporated by reference discusses a number of alternative penetration controlling structures and methodologies which may optionally or advantageously be used if desired for greater accuracy or other reasons now appreciated or hereafter appreciated.

Penetration controlling implies stopping movement of the injection needle and associated parts. This stopping is preferably done in a manner which is done by reducing the speed of the injection assembly. The retraction or return spring serves this by increasingly providing countervailing force against the driving force and momentum of the movable assembly or combination. The apparatus also provides a cushioning of this by using a cushioning member at one or more suitable locations. As shown, this is advantageously done by the cushion, such as cushion washer 457, by the dose controller piece 490 to the extent of elasticity thereof. Elasticity may also be provided by the elasticity of all the components used in the driving and driven injection assembly and supporting materials and parts.

Dispensing of Fluid Medicine to Provide Injection

The driver acts on the plunger directly or indirectly by moving the plunger. The plunger thus acts by displacing the medicine fluid. The displacing of the medicine fluid causes the medicine to be dispensed by conveying the fluid and causing the fluid to perform and exiting through the needle assembly. With the needle already penetrated to the desired penetration depth then the dispensing medicine is administered as desired.

Controlling Dose Administered

The methods according hereto further may include, and preferably do include controlling the dose administered. Controlling the administered dose may be performed in several different potential ways. The current preferred dose controlling is performed as shown and described here and elsewhere in this document.

Figure 24:
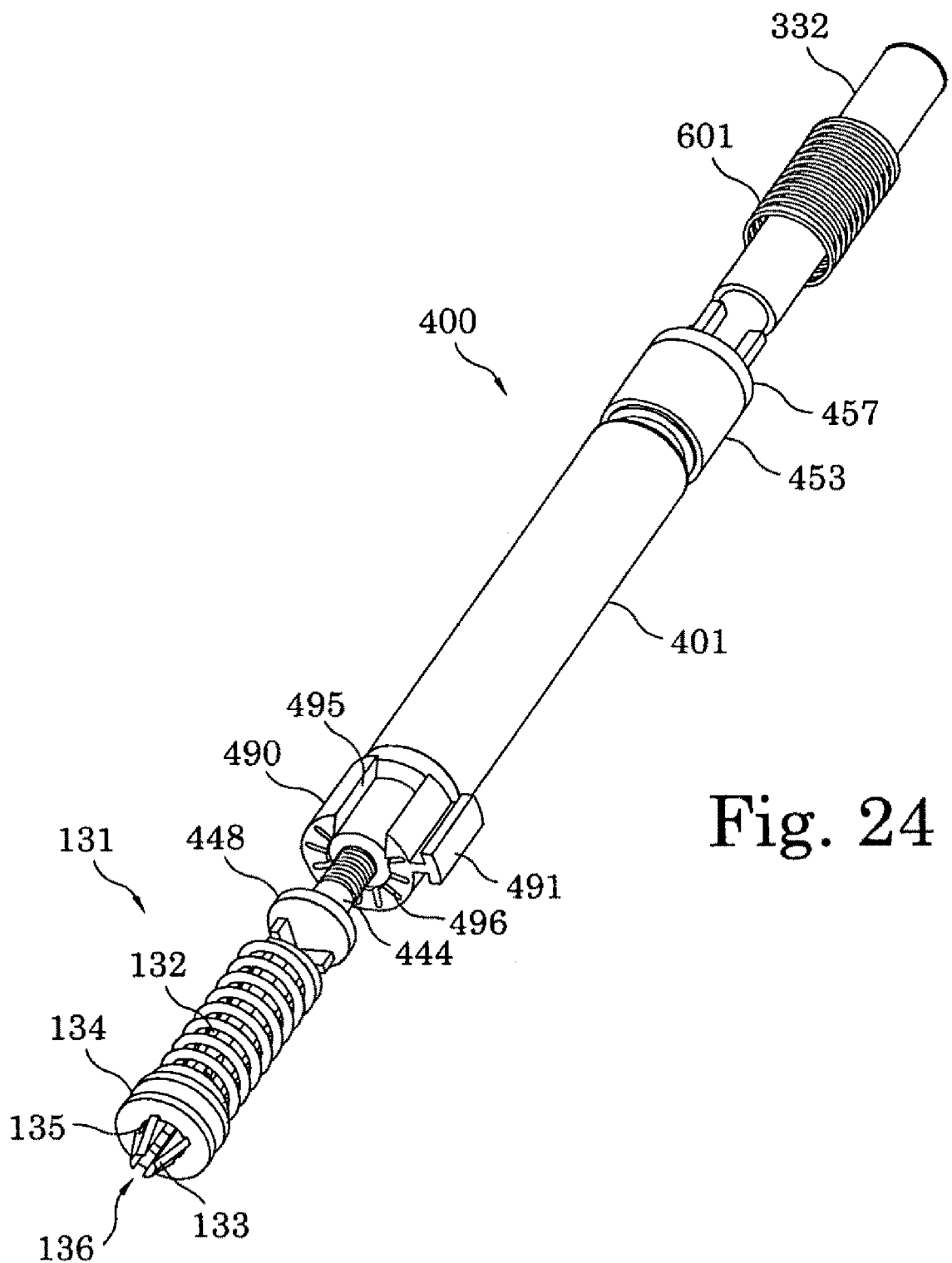
FIG. 24 is an enlarged perspective from a different viewing position of the assembly of FIG. 23 with the needle protector and a portion of the retraction spring included.

During the firing and administrating of the first dose the first driver is stopped by the dose controller piece 490 (see FIGS. 24 and 31. The dose controlling function is illustrated in sectional view by comparing FIGS. 30 and 31. In FIG. 30 the first driver is in a ready and unfired condition. FIG. 31 shows the injector after the firing of the first stage and therein it is shown that the driver center piece has engaged the injection assembly and the plunger 410 has been depressed to displace fluid. The amount of fluid displaced has been determined by the distance between the plunger positions in the respective views.

Sliding Action of Dose Controller

FIG. 17 shows the dose controller 490 preferably has a slide extension 491 which performs by sliding action within the groove or slot 492 (also see FIGS. 13 and 14). This sliding action of the dose controller allows the dose controller to move as part of the injection assembly and to move during travel due to the firing of the first or other stages of drivers equipped with dose controllers.

It is further advantageous because it accomplishes this while also allowing the dose and adjusted length of the injection assembly or travel distant of the driver to vary between injectors or different stages.

The dose controller or controllers are also preferably provided with slide extensions which are retained in the complementary receiving groove to aid in the dose controller removal from the injection assembly as explain further below and elsewhere herein. As shown, this is done using an enlarged slide extension head.

Other dose controllers are possible, which might include a ledge or shelf formed into the inner body piece to which the plunger head is driven by the action of the driver, and stopped by the enlarged driver head meeting said shelf. This method of dose control envisions use of a plunger head that is not enlarged and thereby allows the enlarged driver head to drive down until meeting the arresting shelf.

Retraction of Injection Needle

The preferred methods according hereto also provide for retracting of the injection needle. This retracting action is forced by the retraction spring or other retractor.

In the current preferred constructions the retracting occurs after there is a maintaining of the injection assembly in an extended injection position, such as shown in FIG. 31 wherein the first driver is extended. This maintaining of the longitudinal position at or below a limit provided by the septum wall 271 (FIG. 29) that keeps the plunger contact head in an extended position. The first or other driver keeps the injection assembly extended until the torsional movement performs by repositioning the injection apparatus from one stage (in this case stage one) to a subsequent stage (stage two).

To facilitate the passing of the plunger head under the septum wall the plunger head is advantageously chamfered, rounded or otherwise shaped to facilitate passing of the plunger head, such as torsionally within the apparatus.

Repositioning to Second Stage

Methods according hereto also preferably include moving the injection end into position for a subsequent stage position. As illustrated this is advantageously done in the form of moving into a second stage ready position for administration of a second dose. Also, this is advantageously done by angularly moving a part of the injector relative to another part of the injector to change the condition and move between a first stage angular position to a second stage angular position or positions. Further there is most beneficially two or more angular positions with dosing capabilities.

Angular moving is also done to one or more storage stage positions as is appropriate for the embodiment being used which may have one or more injection assemblies.

Torsional or Angular Latching and Movement

To facilitate proper use of the injection apparatuses and improve practice of preferred methods according hereto, it is advantageous to have torsional or angular latching. The torsional or other angular positioning may be continuous in one direction or another or even both. In the embodiment shown the construction provides for movement in a preferred angular direction.

It is best to appreciate that angular movement, the direction of angular movement, angular latching and angular movement resistance are not necessarily tied or fixed in their respective concepts and may in some various forms of the invention be implemented with different approaches on these aspects of operation and the methods according to the inventions hereof. Explanation will now be made as to pertinent considerations of these aspects of the inventions without implying that such fully cover all potential manners of implementation.

The angular latching function is most appropriately implemented using latches that are associated with the appropriate number of stages and associated stage positions. This latching at predetermined stage latch angular positions helps a user to properly make sure of alignment at the stage positions wherein the injection assembly is adapted to move longitudinally.

In the construction shown and some of the currently preferred methods, the angular movement is limited. Such limiting may be both with regard to a limited path and/or limited sense of direction. For example, the limited path being provided by the collar and the restraining function provided thereby may limit angular movement, the freedom or ease of angular movement, and the sense or direction of angular movement. The limitation of the direction of angular movement may provided in the form of limiting the direction, e.g. clockwise or counterclockwise, as is more appropriately desired. The latching and catching functions described above may be provided by catching the catch piece along the catch surface provided as described above. Other suitable forms of latching may also be used as desired.

Additionally it is possible to perform by providing a resisting effect by using friction by suitably sizing the relatively rotating parts, such as by fitting the parts to a desired degree. Alternatively, the injection apparatus may have multiple teething formed at suitable locations to provide a desired degree of resisting of rotary action or other angular movement between the parts being angularly displaced.

The latching function or angular resisting functions may be used in limiting the direction of angular movement between the two parts which are rotationally or angularly displaced to allow operation hereof.

Application of Torque

The angular movement will typically involve applying angular force, more typically referred to as torque. Such applying of torque or torquing of the respective angularly movable parts of the injection apparatuses is advantageously provided by grasping the upper part in one hand and twisting the torsional assembly or lower part relative thereto. Features described above are specifically provided to facilitate such application of torque, such as the striations 310 and torque fin 320.

Removal of Dose Limiter

The methods of use and performed using preferred apparatuses according hereto may include removing or disengaging of the dose limiter relative to the syringe assembly. This may in another manner of consideration be conceptualized as removing the injection assembly from the dose limiter. This removing or separating of the parts can be done using various techniques shown and/or hereafter developed.

In the illustrated embodiment FIG. 17 in particular is helpful in seeing that the dose limiter may be adapted by having an open side. FIG. 17 further indicates that the syringe assembly can be removed from the dose limiter through such open side which may alternatively be called a side opening.

Second Stage Related Matters

Latching

Latching at Second Stage Position

The latching of the angular movement for movement between the first stage position and the second stage position is as described above.

Injection Assembly

Return of Injection Assembly Into Second Chamber

After angularly positioning the relationship between the upper and lower portions of the injector in the second stage position, then the return spring or other retractor forces the syringe assembly without the dose limiter into a retracted position by retracting the injection assembly.

Second Driver Related Actions

Arming of Second Driver

The arming of the second driver of the second stage for firing is similar to arming the first driver used in the first stage. However, certain differences do exist in the second driver arming which are now explained further.

Figure 32:
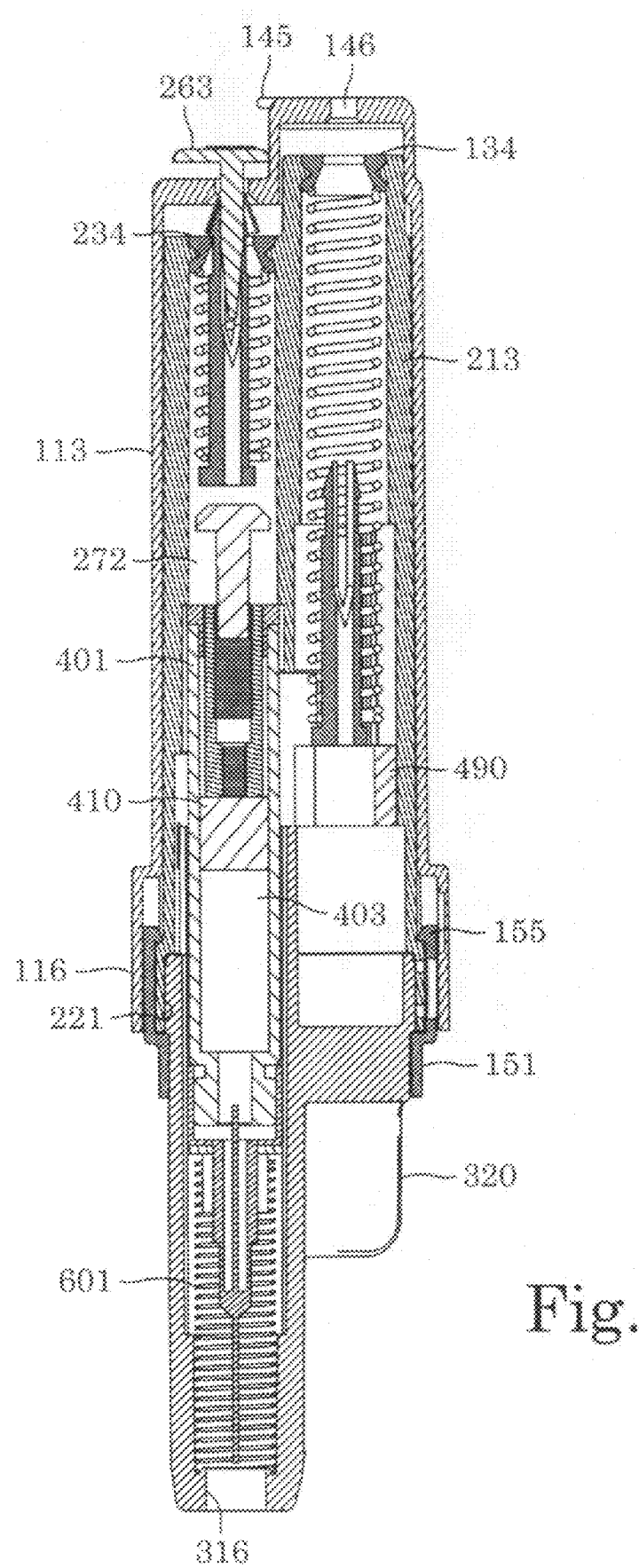
FIG. 32 shows the apparatus of FIG. 29 after the torsional assembly has been rotated to position the injection assembly for administration of a second dose. The dose controller has been removed from the injection assembly and remains in the first chamber.

In the arming of the second driver, the second safety is removed by removing or withdrawing the second safety piece. This involves extracting the second safety as illustrated in FIG. 33. This involves in the illustrated version the passing of the skirt portion 265 out through the safety aperture 235 from the safe condition position of the second safety as illustrated in FIG. 32 to the armed condition shown in FIG. 33.

Triggering of Second Driver

Triggering of the second stage firing by releasing the second stage driver is similar to triggering of the first stage as described above.

Second Insertion of Injection Needle

The second stage driver operates in a similar fashion to the first stage driver. This causes the second stage to effect inserting the injecting needle in a manner as described above in the first stage operation. However, the syringe forming operation is not needed since this was previously performed in the operation of the first stage and the needle is in communication with the fluid reservoir of the ampoule.

Control of Second Dose Penetration Depth

The construction of injector 101 is such that penetration control depth effected for the inserting of the injection needle and associated penetration controlling in similar fashion as indicated for the first stage.

Dispensing and Controlling of Second Dose of Fluid Medicine

Figure 34:
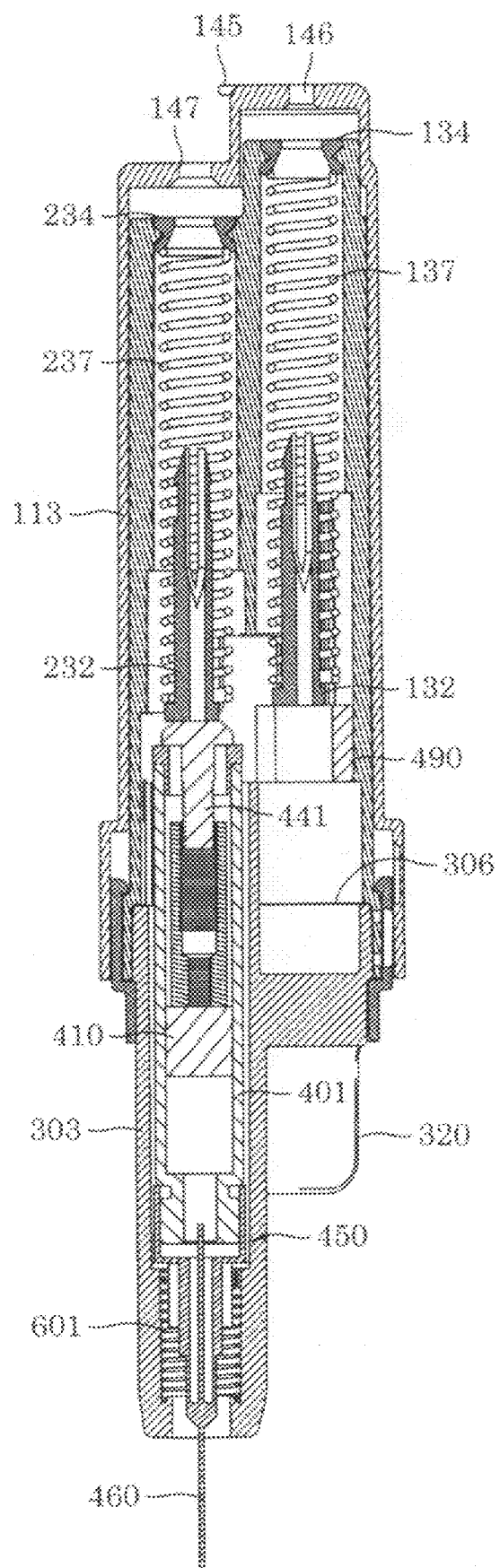
FIG. 34 is similar to FIGS. 32 and 33 except the second driver has been released and the needle has been extended into an injection position to administer a second dose.

FIG. 34 illustrates and helps show that dispensing of the second stage medicine is done in a manner similar to dispensing medication in the first stage. However, the illustrated injector 101 does not use a second dose control element or elements (such as 490). Such a dose controlling may be provided in an alternative embodiment not shown in the illustrations using a second dose controller similar in concept to the first dose controller should an injector be designed to provide more than two doses of medicine. Alternatively, similar to described above a series of ledges with a plunger head without an enlargement and an enlarged driver head that would stop at the desired height and ledge or shelf height may be used.

As shown, the illustrated second stage dispensing is controlled by the extending of the second driver and driving the plunger to a further second administration position deeper in the ampoule.

Positioning of Injection Assembly for Torsional Movement

The injection assembly is maintained in an adequately extended position by the second driver to the keep the injection assembly in the position shown in FIG. 34. This is done at a relative position to allow passing of the plunger contact head under the ledge 284 (see FIG. 29).

Third Stage Operation

Release of Torsional Latch

The release of the injector from the second stage position is a de-latching performed by overcoming the resistance to movement provided by the caught condition and other resistance or resisting action provided by the extensions or recesses 156 and associated recesses indicated above (see 156 in FIG. 9). This occurs in the stage two angular position in a manner similar to that previously described for the stage one angular position.

Application of Torque

The releasing is accompanied by the applying of torque between the upper and lower parts of the injector in a manner similar to or the same as described above.

Retraction of Injection Needle into Sharps Storage Chamber

FIG. 35 illustrates returning of the injection assembly back into the upper part of the injector and into the third chamber 372. Such returning of the injection assembly is advantageously effected by the forcing, such as forcing by retraction or return spring 601 in a retracting function. Such retracting serves to perform a storing of the injection assembly into the third or sharps storage chamber. This then causes positioning of the injection assembly so as to allow safely storing the injection needle in a retracted condition such as shown in FIG. 35.

Reinstallation of Sheath Remover Cap

Methods according hereto may also include reinstalling the sheath 332 in a process which is similar to but opposite in manner and effect to the removing of the sheath made herein above.

In the preferred manners of use, the injector end cap 330 is advantageously done to help provide for protection of the injection extension. As shown, the reinstallation of the sheath 332 is preferably performed by the reinstalling of the sheath remover cap 330.

Reinstallation of Safety End Cap

Methods performed may also include reinstalling the cap 160 adapted to be fitted upon the upper or safety end of the outer body of the upper part of the injector in a manner essentially opposite to the removing done as illustrated in FIGS. 6 and 30.

Disposal of Spent Injector

The spent injector has the sharps device safely stored. This is true at several different levels of safety. The retraction alone of the injection assembly as illustrated in FIG. 35 is safe storage for many, most or all applications as may be found out in the future use of this apparatus or others according to the inventions now known or hereafter developed. However, the benefits of the illustrated embodiment include the added safety levels of having a sheath over the injection needle. Further another level of safety may be provided by having the injection end cap and/or safety end cap on the spent injector.

A still further or substitute level of safety may be provided by using a casing, such as described in the incorporated by reference patent mentioned at the beginning of this document. Any such casing used is advantageously adapted to the size and sufficient to provide the space for receiving the particular injector with which any such casing is used.

The spent injector may then be recycled or destroyed as is considered most appropriate for a particular version or due to regulations or other decision factors appropriate or favored at the time of such disposal.

Methods and Manner of Making

Outer Body Piece(s)

The outer body piece is currently preferably made of polycarbonate polymer. Other suitable materials may also be used.

The preferred manner of making is by molding of the part, such as by injection molding.

Inner Body Piece(s)

The inner body piece is currently preferably made of polycarbonate polymer. Other suitable materials may also be used.

The preferred manner of making is by molding of the part, such as by injection molding.

Safety End Cap

The current preferred cap is nylon. Other suitable materials may also be used.

The preferred manner of making is by molding of the part, such as by injection molding.

Injection End Cap

The current preferred cap is nylon. Other suitable materials may also be used. Similarly the currently preferred sheath is of the same material.

The preferred manner of making is by molding of the part, such as by injection molding.

Torsion Part

The inner body piece is currently preferably made of polycarbonate polymer. Other suitable materials may also be used.

The preferred manner of making is by molding of the part, such as by injection molding.

Coupler

The inner body piece is currently preferably made of polycarbonate polymer. Other suitable materials may also be used.

The preferred manner of making is by molding of the part, such as by injection molding.

Drivers

The drivers use a suitable spring steel which may vary in size or otherwise dependent upon particular force and displacement relationships desired as is known in the art. The springs are formed in any suitable convention manner now known or hereafter developed.

The pronged trigger pieces are preferably made of brass and are received against steel ferrules.

Second Safety

The current preferred second safety is nylon. Other suitable materials may also be used.

The preferred manner of making is by molding of the part, such as by injection molding.

Injection Assembly

The injection assembly preferably includes a medicine ampoule or suitable medicine storage container or similar part. As shown, the manner of making the injection apparatus includes selecting or making an ampoule which includes a medicine container. The selecting or making includes selecting a container by choosing a container made of material or materials which are relatively unaffected by the medicine which is being stored therein. In many cases the choosing of a suitable container will be to have a glass ampoule container. This is currently preferred because epinephrine and other medicines are frequently less affected by storing the medicine in glass containers.

The choosing of a suitable material may include other materials found suitable. Plastic may in some cases be preferred for durability under conditions where shock may be experienced. For example, wartime conditions may lead to use of relatively rugged syringe materials so that a medic, soldier or other military or support personnel who are at risk may survive an explosion nearby, or being otherwise shocked or thrown around and yet have the injection device and medicine still be intact to allow treatment of the carrying user or used for administration to others.

The choosing may also include other desired materials for the containing of the medicine in the selected or chosen medicine ampoule, syringe or other container or containers.

The current preferred methods of making include selecting a medicine ampoule which is sealed or includes sealing of the ampoule after instilling the medicine therein. This is most easily done by choosing an ampoule which has a sealed injection needle end. The ampoule is also advantageously chosen to include a seal which is consistent with the contained medicine and is not effectively corroded thereby within the period of the suitable shelf life and a protection period thereafter.

The preferred selecting also advantageously includes an ampoule or syringe which is provided with a displacing element. As shown as is typical at this time, such a displacing element is in the form of a movable plunger positioned to move within the ampoule to displace medicine therefrom.

It may also be suitable to have a fully sealed container that uses a peristaltically displaceable portion which is squeezed, rolled or otherwise distorted to displace medicine therefrom.

The making also preferably includes attaching or otherwise connecting a driver contact. The driver contact is preferably chosen to have a durable head such as a polycarbonate, other hard plastic or metallic head which is suitable for taking the impact of the driver.

The making of the injection assembly also may include attaching into the plunger assembly an adjustable element. Such adjustable element may include adjustment to affect the accuracy or amount of displaced medicine to be an accurate amount. As shown, the injection assembly is made using an adjustable element which is aluminum, polycarbonate or other hard plastic or suitable metallic materials.

Return Spring

Return spring 601 which acts as a retractor may be made in a suitable fashion now known or hereafter developed in the art of spring production to provide the performance desired. Such shall depend upon the specifics of a particular injector and the size and specific.

Miscellaneous

Various portions and components of apparatuses within the scope of the inventions, including for example, structural components, may be formed by one or more various suitable manufacturing processes known to those in the relevant art or arts. These may include the arts of metal working, thermoplastics and injection molding of thermoplastics. Similarly, various portions and components of apparatuses within the scope of the inventions can be made from suitable materials known to those in the arts of thermoplastics and injection molding of thermoplastics. It is to be understood, however, that various portions and components of apparatuses within the scope of the inventions may be formed by one or more various suitable manufacturing processes known to those in arts other than those specifically mentioned herein, and/or by one or more processes or means not yet known but hereafter developed.

Interpretation Notes

The above description has set out various features, functions, methods and other aspects of the inventions. This has been done with regard to the currently preferred embodiments thereof. Time and further development may change the manner in which the various aspects are implemented. Such aspects may further be added to by the language of the claims which are incorporated by reference hereinto as originally filed.

The scope of protection accorded the inventions as defined by the claims is not intended to be necessarily limited to the specific sizes, shapes, features or other aspects of the currently preferred embodiments shown and described. The claimed inventions may be implemented or embodied in other forms while still being within the concepts shown, described and claimed herein. Also included are equivalents of the inventions which can be made without departing from the scope of concepts properly protected hereby.

I claim:

1. An apparatus for injecting multiple doses of medicine having:
    a body with an exterior surface for being held by a user;
    plural chambers within the body;
    at least one medicine ampoule within the body for holding a fluid medicine therein;
    a plunger displaceable to dispense medicine from the one ampoule;
    plural drivers mounted within the body and configured to independently engage and/or displace the plunger to dispense medicine from the one ampoule plural times; and
    at least one injection needle which is movable between retracted and extended positions, in said extended position the at least one injection needle being extended to allow penetration into flesh to inject medicine into a recipient provided from said ampoule.

2. The apparatus according to claim 1 and further including at least one retractor for biasing the at least one injection needle into a retracted position.

3. The apparatus according to claim 1 and further including at least one storage chamber within the body to allow retraction of the at least one injection needle.

4. The apparatus according to claim 1 and further including an inner body within said body which is adapted to move longitudinally with respect to the body.

5. The apparatus according to claim 1 and further including an inner body within said body which is adapted to move longitudinally with respect to the body to serve in triggering the apparatus.

6. The apparatus according to claim 1 and further including at least one dose controller which controls depression of the plunger to allow dispensing medicine from the ampoule plural times.

7. The apparatus according to claim 1 and further including at least one penetration controller to help control depth of penetration by the at least one injection needle when extended.

8. An apparatus for injecting multiple doses of medicine having:
    a body with an exterior surface for being held by a user;
    plural chambers within the body;
    at least one injector within the body adapted for holding fluid medicine;
    at least first and second drivers mounted within at least two of said plural chambers and configured to independently engage the one injector into extended positions to dispense medicine into a recipient; and
    whereby multiple doses may be administered with the at least one injector properly positioned relative to the first and second drivers.

9. The apparatus according to claim 8 and further including at least one retractor for biasing the at least one injector into retracted positions at least partially into said plural chambers.

10. The apparatus according to claim 8 and further including at least one storage chamber within the body to allow retraction of the at least one injector therein.

11. The apparatus according to claim 8 and further including an inner body and an outer body forming parts of said body, said inner body and said outer body being adapted for relative movement to allow triggering of the apparatus to administer injections.

12. The apparatus according to claim 8 and further including at least one dose controller which controls dispensing of medicine from the injector.

13. The apparatus according to claim 8 and further including at least one penetration controller to help control depth of penetration of the injector into the recipient when extended.

14. An apparatus for injecting multiple doses of medicine having:
    a body with an exterior surface for being held by a user;
    plural chambers within the body;
    at least one medicine ampoule within the body for holding a fluid medicine therein, said at least one medicine ampoule having a plunger which may be displaced to dispense medicine from the ampoule;
    plural drivers mounted within the body and configured to independently engage the plunger and displace the plunger to dispense medicine from the at least one ampoule plural times;
    at least one injection needle which is movable between retracted and extended positions, in said extended position the at least one injection needle being extended to allow penetration into flesh to inject medicine into a recipient provided from said ampoule;
    a movable portion connected to move relative to the body into plural positions, said plural positions including positions relative to said plural chambers to allow said plural drivers to independently engage the plunger.

15. The apparatus according to claim 14 and wherein said movable portion includes at least one injector barrel through which the at least one injection needle moves longitudinally to extend into an extended position.

16. The apparatus according to claim 14 and further including at least one storage chamber within the body to allow retraction of the at least one injection needle.

17. The apparatus according to claim 14 and further including an inner body within said body which is adapted to move longitudinally with respect to the body.

18. The apparatus according to claim 14 and further including an inner body within said body which is adapted to move longitudinally with respect to the body to serve in triggering the apparatus.

19. The apparatus according to claim 14 and further including at least one dose controller which is removable relative to the at least one medicine ampoule when the movable portion is moved.

20. The apparatus according to claim 14 and further including at least one dose controller which controls depression of the plunger to control dispensing of medicine from the ampoule to allow plural doses, said at least one dose controller being removable relative to the plunger when the movable portion is moved.

* * * * *

UNITED STATES PATENT AND TRADEMARK OFFICE
CERTIFICATE OF CORRECTION

PATENT NO. : 8,366,682 B2  Page 1 of 1
APPLICATION NO. : 12/380954
DATED : February 5, 2013
INVENTOR(S) : Ronald E. Wyrick It is certified that error appears in the above-identified patent and that said Letters Patent is hereby corrected as shown below:

Title Page 2, (56) References Cited, Other Publications – Replace
"WO PCT/US05/43309 Search Report, Jun. 22, 2005,
Washington Biotech Corporation" with
--WO PCT/US05/43309 Search Report, Jun. 22, 2006,
Washington Biotech Corporation--

In the Specification

Column 19, line 46 – Replace "as explain" with --as explained--

Column 20, line 55 – Replace "may provided" with --may be provided--

Signed and Sealed this
Twenty-sixth Day of November, 2013

Margaret A. Focarino
*Commissioner for Patents of the United States Patent and Trademark Office*